United States Patent [19]
Gewirtz et al.

[11] Patent Number: 5,618,709
[45] Date of Patent: Apr. 8, 1997

[54] ANTISENSE OLIGONUCLEOTIDES SPECIFIC FOR STK-1 AND METHOD FOR INHIBITING EXPRESSION OF THE STK-1 PROTEIN

[75] Inventors: Alan M. Gewirtz, Philadelphia, Pa.; Donald Small; Curt I. Civin, both of Baltimore, Md.

[73] Assignees: University of Pennsylvania, Philadelphia, Pa.; The Johns Hopkins University, Baltimore, Md.

[21] Appl. No.: 183,211

[22] Filed: Jan. 14, 1994

[51] Int. Cl.$^6$ .............. C12N 15/00; C07H 21/04
[52] U.S. Cl. .......... 435/172.3; 536/24.5; 135/34
[58] Field of Search ............... 536/23.2, 24.5; 435/172.3, 320.1; 424/93.1; 514/44

[56] References Cited

U.S. PATENT DOCUMENTS

| | | | |
|---|---|---|---|
| 5,087,617 | 2/1992 | Smith | 514/44 |
| 5,098,890 | 3/1992 | Gewirtz et al. | |
| 5,270,458 | 12/1993 | Lemischka | 536/23.5 |
| 5,271,941 | 12/1993 | Cho-Chung | |
| 8,185,438 | 2/1993 | Lemischka | 536/23.2 |

FOREIGN PATENT DOCUMENTS 9222303  12/1992  WIPO .
9309789  5/1993  WIPO .

OTHER PUBLICATIONS

Smith et al (1986) Aust.N.Z.J. Med. 16, 39–42.
Park et al (1980) Blood 55, 595–601.
Gustavsson et al (1984) Canc. Res. 44, 4648–4652.
Veerman et al (1990) Brit.J. Hemat. 74, 381–384.
van der Krol et al (1988) Biotechniques 6, 958–976.
Tseng et al (1994) Cancer Gene Therapy 1, 65–71.
Lyman et al (1993) Blood, vol. 82 (Suppl.1), 87a.
Rosnet et al (1993) Blood vol. 82(4), 1110–1119.
Matthews et al (1991) Cell 65, 1143–1152.
Lyman et al (1993) Oncogene 8, 815–822.
Rosnet et al (1991) Oncogene 6, 1641–1650.

*Primary Examiner*—Deborah Crouch
*Attorney, Agent, or Firm*—Seidel, Gonda, Lavorgna & Monaco, P.C.

[57] ABSTRACT

Oligonucleotides are provided having a nucleotide sequence complementary to at least a portion of the mRNA transcript of the STK-1 gene. These "antisense" oligonucleotides are hybridizable to the STK-1 mRNA transcript. Such oligonucleotides are useful in treating neoplastic diseases characterized by activation of STK-1 gene expression. The oligonucleotides are also useful as bone marrow purging agents in the treatment of leukemia and metastasized neoplasms.

15 Claims, 9 Drawing Sheets

FIG. 1A

```
          CGAGGCGGCATCCGAGGGCTGGGCCGGCGCCCTGGGGGACCCCGGGCTCCGGAGGCC    57
  1   M  P  A  L  A  R  D  A  G  T  V  P  L  L  V  V  F  S  A  M
      ATGCCGGCGTTGGCGCGCGACGCGGGCACCGTGCCGCTGCTCGTTGTTTTTCTGCAATG   117
 21   I  F  G  T  I  T  N  Q  D  L  P  V  I  K  C  V  L  I  N  H
      ATATTTGGGACTATTACAAATCAAGATCTGCCTGTGATCAAGTGTGTTTTAATCAATCAT   177
 41   K  N  N  D  S  S  V  G  K  S  S  S  Y  P  M  V  S  E  S  P
      AAGAACAATGATTCATCAGTGGGGAAGTCATCATCATATCCCATGGTATCAGAATCCCCG   237
 61   E  D  L  G  C  A  L  R  P  Q  S  S  G  T  V  Y  E  A  A  A
      GAAGACCTCGGGTGTGCGTTGAGACCCCAGAGCTCAGGGACAGTGTACGAAGCTGCCGCT   297
 81   V  E  V  D  V  S  A  S  I  T  L  Q  V  L  V  D  A  P  G  N
      GTGGAAGTGGATGTATCTGCTTCCATCACACTGCAAGTGCTGGTCGATGCCCCAGGGAAC   357
101   I  S  C  L  W  V  F  K  H  S  S  L  N  C  Q  P  H  F  D  L
      ATTTCCTGTCTCTGGGTCTTTAAGCACAGCTCCCTGAATTGCCAGCCACATTTTGATTTA   417
121   Q  N  R  G  V  V  S  M  V  I  L  K  M  T  E  T  Q  A  G  E
      CAAAACAGAGGAGTTGTTTCCATGGTCATTTTGAAAATGACAGAAACCCAAGCTGGAGAA   477
141   Y  L  L  F  I  Q  S  E  A  T  N  Y  T  I  L  F  T  V  S  I
      TACCTACTTTTTATTCAGAGTGAAGCTACCAATTACACAATATTGTTTACAGTGAGTATA   537
161   R  N  T  L  L  Y  T  L  R  R  P  Y  F  R  K  M  E  N  Q  D
      AGAAATACCCTGCTTTACACATTAAGAAGACCTTACTTTAGAAAAATGGAAAACCAGGAC   597
181   A  L  V  C  I  S  E  S  V  P  E  P  I  V  E  W  V  L  C  D
      GCCCTGGTCTGCATATCTGAGAGCGTTCCAGAGCCGATCGTGGAATGGGTGCTTTGCGAT   657
201   S  Q  G  E  S  C  K  E  E  S  P  A  V  V  K  K  E  E  K  V
      TCACAGGGGGAAAGCTGTAAAGAAGAAAGTCCAGCTGTTGTTAAAAAGGAGGAAAAAGTG   717
221   L  H  E  L  F  G  T  D  I  R  C  C  A  R  N  E  L  G  R  E
      CTTCATGAATTATTTGGGACGGACATAAGGTGCTGTGCCAGAAATGAACTGGGCAGGGAA   777
241   C  T  R  L  F  T  I  D  L  N  Q  T  P  Q  T  T  L  P  Q  L
      TGCACCAGGCTGTTCACAATAGATCTAAATCAAACTCCTCAGACCACATTGCCACAATTA   837
261   F  L  K  V  G  E  P  L  W  I  R  C  K  A  V  H  V  N  H  G
      TTTCTTAAAGTAGGGGAACCCTTATGGATAAGGTGCAAAGCTGTTCATGTGAACCATGGA   897
281   F  G  L  T  W  E  L  E  N  K  A  L  E  E  G  N  Y  F  E  M
      TTCGGGCTCACCTGGGAATTAGAAAACAAAGCACTCGAGGAGGGCAACTACTTTGAGATG   957
301   S  T  Y  S  T  N  R  T  M  I  R  I  L  F  A  F  V  S  S  V
      AGTACCTATTCAACAAACAGAACTATGATACGGATTCTGTTTGCTTTTGTATCATCAGTG  1017
321   A  R  N  D  T  G  Y  Y  T  C  S  S  S  K  H  P  S  Q  S  A
      GCAAGAAACGACACCGGATACTACACTTGTTCCTCTTCAAAGCATCCCAGTCAATCAGCT  1077
341   L  V  T  I  V  E  K  G  F  I  N  A  T  N  S  S  E  D  Y  E
      TTGGTTACCATCGTAGAAAAGGGATTTATAAATGCTACCAATTCAAGTGAAGATTATGAA  1137
361   I  D  Q  Y  E  E  F  C  F  S  V  R  F  K  A  Y  P  Q  I  R
      ATTGACCAATATGAAGAGTTTTGTTTTTCTGTCAGGTTTAAAGCCTACCCACAAATCAGA  1197
381   C  T  W  T  F  S  R  K  S  F  P  C  E  Q  K  G  L  D  N  G
      TGTACGTGGACCTTCTCTCGAAAATCATTTCCTTGTGAGCAAAAGGGTCTTGATAACGGA  1257
401   Y  S  I  S  K  F  C  N  H  K  H  Q  P  G  E  Y  I  F  H  A
      TACAGCATATCCAAGTTTTGCAATCATAAGCACCAGCCAGGAGAATATATATTCCATGCA  1317
421   A  E  N  D  D  A  Q  F  T  K  M  F  T  L  N  I  R  R  K  P
      GAAAATGATGATGCCCAATTTACCAAAATGTTCACGCTGAATATAAGAAGGAAACCTCAA  1377
441   Q  V  L  A  E  A  S  A  S  Q  A  S  C  F  S  D  G  Y  P  L
      CAGGTGCTCGCAGAAGCATCGGCAAGTCAGGCGTCCTGTTTCTCGGATGGATACCCATTA  1437
461   S  W  T  W  K  K  C  S  D  K  S  P  N  C  T  E  E  I  T  E
      TCTTGGACCTGGAAGAAGTGTTCAGACAAGTCTCCCAACTGCACAGAAGAGATCACAGAA  1497
481   G  V  W  N  R  K  A  N  R  K  V  F  G  Q  W  V  S  S  S  T
      GGAGTCTGGAATAGAAAGGCTAACAGAAAAGTGTTTGGACAGTGGGTGTCGAGCAGTACT  1557
501   L  N  M  S  E  A  I  K  G  F  L  V  K  C  C  A  Y  N  S  L
      CTAAACATGAGTGAAGCCATAAAAGGGTTCCTGGTCAAGTGCTGTGCATACAATTCCCTT  1617
521   G  T  S  C  E  T  I  L  L  N  S  P  G  P  F  P  F  I  Q  D
      GGCACATCTTGTGAGACGATCCTTTTAAACTCTCCAGGCCCCTTCCCTTTCATCCAAGAC  1677
```

FIG. 1B

| | | |
|---|---|---|
| 541 | N I S F Y A T I G V C L L F I V V L T L | |
| | AACATCTCATTCTATGCAACAATTGGTGTTTGTCTCCTCTTCATTGTCGTTTTAACCCTG | 1737 |
| 561 | L I C H K Y K K Q F R Y E S Q L Q M V Q | |
| | CTAATTTGTCACAAGTACAAAAAGCAATTTAGGTATGAAAGCCAGCTACAGATGGTACAG | 1797 |
| 581 | V T G S S D N E Y F Y V D F R E Y E Y D | |
| | GTGACCGGCTCCTCAGATAATGAGTACTTCTACGTTGATTTCAGAGAATATGAATATGAT | 1857 |
| 601 | L K W E F P R E N L E F G K V L G S G A | |
| | CTCAAATGGGAGTTTCCAAGAGAAAATTTAGAGTTTGGGAAGGTACTAGGATCAGGTGCT | 1917 |
| 621 | F G K V M N A T A Y G I S K T G V S I Q | |
| | TTTGGAAAAGTGATGAACGCAACAGCTTATGGAATTAGCAAAACAGGAGTCTCAATCCAG | 1977 |
| 641 | V A V K M L K E K A D S S E R E A L M S | |
| | GTTGCCGTCAAAATGCTGAAAGAAAAAGCAGACAGCTCTGAAAGAGAGGCACTCATGTCA | 2037 |
| 661 | E L K M M T Q L G S H E N I V N L L G A | |
| | GAACTCAAGATGATGACCCAGCTGGGAAGCCACGAGAATATTGTGAACCTGCTGGGGGCG | 2097 |
| 681 | C T L S G P I Y L I F E Y C C Y G D L L | |
| | TGCACACTGTCAGGACCAATTTACTTGATTTTTGAATACTGTTGCTATGGTGATCTTCTC | 2157 |
| 701 | N Y L R S K R E K F H R T W T E I F K E | |
| | AACTATCTAAGAAGTAAAAGAGAAAAATTTCACAGGACTTGGACAGAGATTTTCAAGGAA | 2217 |
| 721 | H N F S F Y P T F Q S H P N S S M P G S | |
| | CACAATTTCAGTTTTTACCCCACTTTCCAATCACATCCAAATTCCAGCATGCCTGGTTCA | 2277 |
| 741 | R E V Q I H P D S D Q I S G L H G N S F | |
| | AGAGAAGTTCAGATACACCCGGACTCGGATCAAATCTCAGGGCTTCATGGGAATTCATTT | 2337 |
| 761 | H S E D E I E Y E N Q K R L E E E D L | |
| | CACTCTGAAGATGAAATTGAATATGAAAACCAAAAAAGGCTGGAAGAAGAGGAGGACTTG | 2397 |
| 781 | N V L T F E D L L C F A Y Q V A K G M E | |
| | AATGTGCTTACATTTGAAGATCTTCTTTGCTTTGCATATCAAGTTGCCAAAGGAATGGAA | 2457 |
| 801 | F L E F K S C V H R D L A R N V L V T | |
| | TTTCTGGAATTTAAGTCGTGTGTTCACAGAGACCTGGCCGCCAGGAACGTGCTTGTCACC | 2517 |
| 821 | H G K V V K I C D F G L A R D I M S D S | |
| | CACGGGAAAGTGGTGAAGATATGTGACTTTGGATTGGCTCGAGATATCATGAGTGATTCC | 2577 |
| 841 | N Y V V R G N A R L P V K W M A P E S L | |
| | AACTATGTTGTCAGGGGCAATGCCCGTCTGCCTGTAAAATGGATGGCCCCCGAAAGCCTG | 2637 |
| 861 | F E G I Y T I K S D V W S Y G I L L W E | |
| | TTTGAAGGCATCTACACCATTAAGAGTGATGTCTGGTCATATGGAATATTACTGTGGGAA | 2697 |
| 881 | I F S L G V N P Y P G I P V D A N F Y K | |
| | ATCTTCTCACTTGGTGTGAATCCTTACCCTGGCATTCCGGTTGATGCTAACTTCTACAAA | 2757 |
| 901 | L I Q N G F K M D Q P F Y A T E E I Y I | |
| | CTGATTCAAAATGGATTTAAAATGGATCAGCCATTTTATGCTACAGAAGAAATATACATT | 2817 |
| 921 | I M Q S C W A F D S R K R P S F P N L T | |
| | ATAATGCAATCCTGCTGGGCTTTTGACTCAAGGAAACGGCCATCCTTCCCTAATTTGACT | 2877 |
| 941 | S F L G C Q L A D A E E A M Y Q N V D G | |
| | TCGTTTTTAGGATGTCAGCTGGCAGATGCAGAAGAAGCGATGTATCAGAATGTGGATGGC | 2937 |
| 961 | R V S E C P H T Y Q N R R P F S R E M D | |
| | CGTGTTTCGGAATGTCCTCACACCTACCAAAACAGGCGACCTTTCAGCAGAGAGATGGAT | 2997 |
| 981 | L G L L S P Q A Q V E D S | |
| | TTGGGGCTACTCTCTCCGCAGGCTCAGGTCGAAGATTCGTAGAGGAACAATTTAGTTTTA | 3057 |
| | AGGACTTCATCCCTCCACCTATCCCTAACAGGCTGTAGATTACCAAAACAAGATTAATTT | 3117 |
| | CATCACTAAAAGAAAATCTATTATCAACTGCTGCTTCACCAGACTTTTCTCTAGAAGCCG | 3177 |
| | TCTGCGTTTACTCTTGTTTTCAAAGGGACTTTTGTAAAATCAAATCATCCTGTCACAAGG | 3237 |
| | CAGGAGGAGCTGATAATGAACTTTATTGGAGCATTGATCTGCATCCAAGGCCTTCTCAGG | 3297 |
| | CCGGCTTGAGTGAATTGTGTACCTGAAGTACAGTATATTCTTGTAAATACATAAAACAAA | 3357 |
| | AGCATTTTGCTAAGGAGAAGCTAATATGATTTTTTAAGTCTATGTTTTAAAATAATATGT | 3417 |
| | AAATTTTTCAGCTATTTAGTGATATATTTTATGGGTGGGAATAAAATTTCTACTACAGA | 3476 |

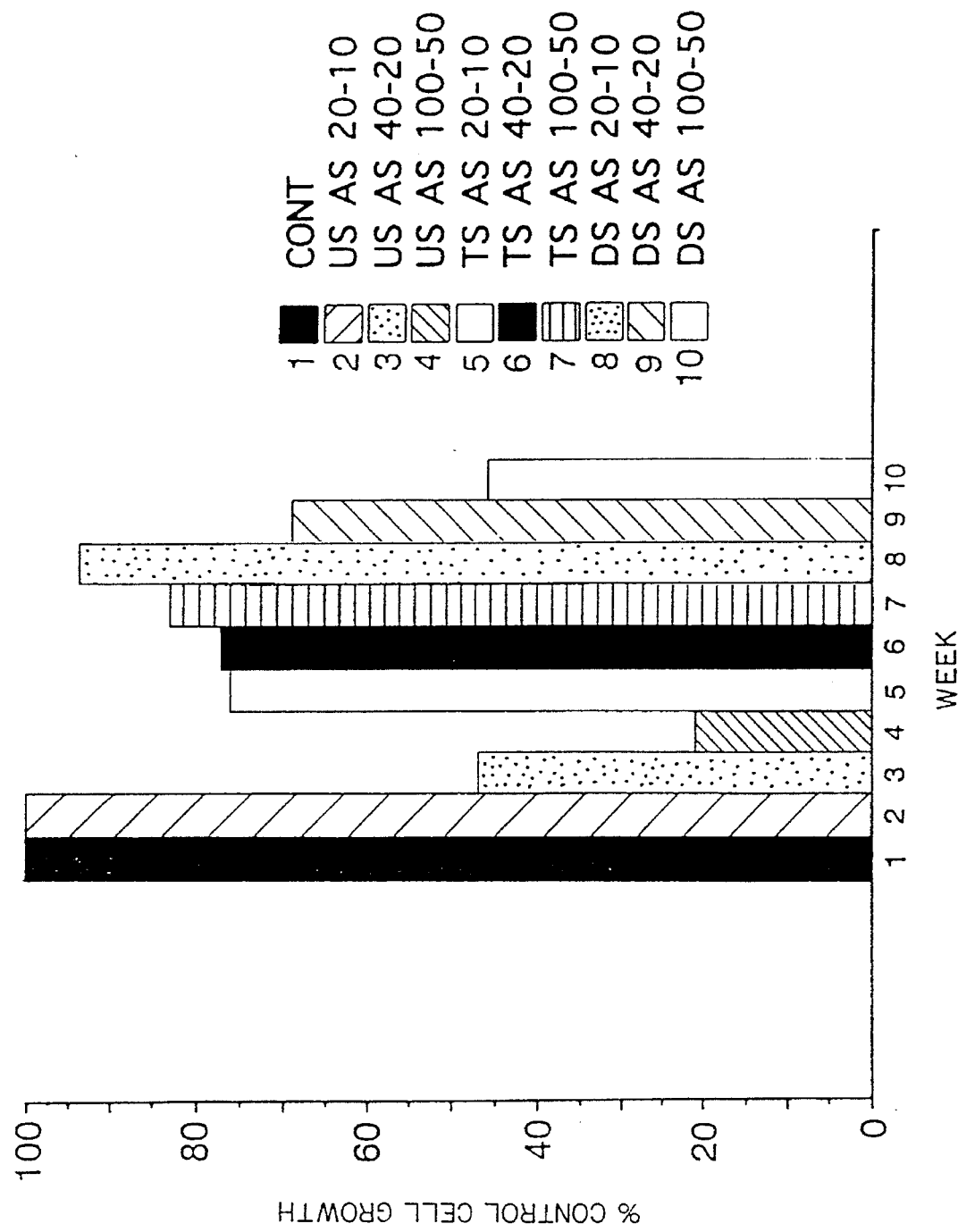

ANTISENSE OLIGONUCLEOTIDES SPECIFIC FOR STK-1 AND METHOD FOR INHIBITING EXPRESSION OF THE STK-1 PROTEIN

REFERENCE TO GOVERNMENT GRANT

The invention described herein was supported in part by the National Institutes of Health grants CA36896, CA54384 and CA51083. The United States Government has certain rights in the invention.

FIELD OF THE INVENTION

The invention relates to antisense oligonucleotides, in particular to antisense oligonucleotides to the STK-1 gene, and the use of such oligonucleotides to inhibit proliferation of certain cells.

BACKGROUND OF THE INVENTION

The human hematopoietic system is composed of a wide variety of red and white blood cell types that differ in morphology, migratory destination and physiological function. Mature red blood cells which are non-nucleated are called erythrocytes. Mature white blood cells occur with a greater diversity of cells types. Types of mature white blood cells include B-lymphocytes, T-lymphocytes, platelets, monocytes, macrophages, megakaryocytes, neutrophils, eosinophils, basophiles, and mast cells. The cells of the hematopoietic system were reviewed by Dexter, et al., *Ann. Rev. Cell Biol.* 3 423–441 (1987).

Proliferation and differentiation of hematopoietic cells are regulated by several growth factors. Hematopoietic growth factors interact with specific cell surface receptors to activate signal transduction pathways in the cytoplasm and nucleus. The activation of cell surface receptors affects the expression of proliferation-and/or differentiation-associated genes (Clark & Kamen, *Science* 236:16 (1987); C.A. Seif, *J. Clin. Invest.* 79:1549 (1987); N. A. Nicola, *Annu. Rev. Biochem* 58:45 (1989); Ullrich and Schlessinger, *Cell*, 61:203 (1990)). Ligand-activated hematopoietic growth factor receptors possess intrinsic tyrosine kinase activity or associate with intracellular tyrosine kinases (Ullrich and Schlessinger, *Cell*, 61:203 (1990); Cross and Dexter, *Cell* 64:271 (1991)). In turn, the tyrosine kinase activity leads to phosphorylation of tyrosine residues of other cytoplasmic proteins (Isfort and Ihle, *Growth Factors* 2:213 (1990); Miyazawa et al., *Exp. Hematol.* 19:1110 (1991) in both normal and leukemic cells (Cantley et al., *Cell* 64:281 (1991)).

The role of hematopoietic growth factors is complex and presently not well understood. Most models for the development of mature blood cells from more primitive progenitor stem cells are based on in vitro studies. Hence, the molecular components that mediate the in vivo hematopoietic development behavior of the most immature hematopoietic stem cells are largely unknown.

The best known and characterized growth factors, thus far, primarily affect the more restricted lineage progenitor cells. The growth factors that affect both mature cells and stem cells may affect a small or a large number of mature cells. However, there are growth factors which appear to only affect immature cells. A protein tyrosine kinase (PTK) which may affect only stem cells without any effect on mature cells has recently been discovered in mice. The PTK for this ligand has been characterized as murine fetal liver kinase-1 (FLK-1 or FLK-2), and is described in U.S. Pat. No. 5,185,438 issued Feb. 9, 1993 to Lemischka. FLK-2 is expressed in populations of mice primitive stem/progenitor cells. Another related protein is the FLT3 protein from mouse placenta and mouse testes. FLT3 is expressed hematopoietic cells present in lymph nodes, spleen, thymus and fetal liver. FLT3 plays an important role in early hematopoietic stem cell development.

SUMMARY OF THE INVENTION

The invention provides antisense oligonucleotides specific for STK-1, and pharmaceutical compositions thereof. The pharmaceutical composition comprises a pharmaceutically acceptable carrier and an antisense oligonucleotide specific for STK-1, as hereinafter defined.

The invention also provides an in vivo or ex vivo method for inhibiting the growth of or killing leukemic cells and other tumors which express STK-1. The method comprises administering to an individual or cells harvested from the individual an effective amount of a STK-1 antisense oligonucleotide.

The invention further provides a method of purging from bone marrow neoplastic cells which may express STK-1. Bone marrow aspirated from an individual afflicted with a hematologic neoplasm is treated with an effective amount of STK-1 antisense oligonucleotide. The thus-treated cells are then returned to the body of the afflicted individual.

According to another embodiment, the invention provides an artificially-constructed gene comprising a transcriptional promotor segment and a segment containing STK-1 DNA in inverted orientation such that transcription of the artificially-constructed gene produces RNA complementary to a portion of an mRNA transcript of the STK-1 gene. The gene may be introduced into neoplastic cells which may express STK-1 to inhibit the proliferation of those cells. The artificially-constructed gene may be introduced into the neoplastic cells by, for example, transfection, transduction with a viral vector, or microinjection.

Definitions

A "primitive hematopoietic cell" is defined as a totipoietic cell capable of reconstituting all hematopoietic blood cells in vivo.

An "antisense oligonucleotide specific for STK-1" or "STK-1 antisense oligonucleotide" is an oligonucleotide having a sequence (i) capable of forming a stable triplex with a portion of the STK-1 gene, or (ii) capable of forming a stable duplex with a portion of an mRNA transcript of the STK-1 gene.

The term "oligonucleotide" as used herein includes linear oligomers of natural or modified monomers or linkages, including deoxyribonucleotides, ribonucleosides, α-enantiomeric forms thereof, polyamide nucleic acids, and the like, capable of specifically binding to a target polynucleotide by way of a regular pattern of monomer-to-monomer interactions, such as Watson-Crick type of base pairing, Hoogsteen or reverse Hoogsteen types of base pairing, or the like. Usually, monomers are linked by phosphodiester bonds or analogs thereof to form oligonucleotides ranging in size from a few monomeric units, e.g., 3–4, to several hundreds of monomeric units. Analogs of phosphodiester linkages include: phosphorothioate, phosphorodithioate, phosphoroselenoate, phosphorodiselenoate, phosphoroanilothioate, phosphoranilidate, phosphoramidate, and the like, as more fully described below. As used herein, "nucleoside" includes the natural nucleosides, including 2'-deoxy and 2'-hydroxyl forms, e.g., as described in Kornberg et al., *DNA Replication*, 2nd Ed. (Freeman, San Francisco, 1992).

"Analogs" in reference to nucleosides includes synthetic nucleosides having modified base moieties and/or modified sugar moieties, e.g., described generally by Scheit, *Nucleotide Analogs* (John Wiley, New York, 1980). Such analogs include synthetic nucleosides designed to enhance binding properties, e.g., duplex or triplex stability, specificity, or the like.

The term "phosphorothioate oligonucleotide" means an oligonucleotide wherein one or more of the internucleotide linkages is a phosphorothioate group,

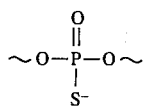

as opposed to the phosphodiester group

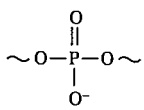

which is characteristic of unmodified oligonucleotides.

By "alkylphosphonate oligonucleoside" is meant an oligonucleotide wherein one or more of the internucleotide linkages is an alkylphosphonate group,

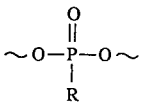

wherein R is an alkyl group, preferably methyl or ethyl.

"Stability" in reference to duplex or triplex formation roughly means how tightly an antisense oligonucleotide binds to its intended target sequence; more precisely, it means the free energy of formation of the duplex or triplex under physiological conditions. Melting temperature under a standard set of conditions, e.g., as described below, is a convenient measure of duplex and/or triplex stability. Preferably, antisense oligonucleotides of the invention are selected that have melting temperatures of at least 50° C. under the standard conditions set forth below. Thus, under physiological conditions and the preferred concentrations, duplex or triplex formation will be substantially favored over the state in which the antisense oligonucleotide and its target are dissociated. It is understood that a stable duplex or triplex may in some embodiments include mismatches between base pairs and/or among base triplets in the case of triplexes. Preferably, antisense oligonucleotides of the invention form perfectly matched duplexes and/or triplexes with their target polynucleotides.

The term "downstream" when used in reference to a direction along a nucleotide sequence means the 5' to 3' direction. Similarly, the term "upstream" means the 3' to 5' direction.

The term "STK-1 mRNA transcript" means the presently known mRNA transcript of the STK-1 (SEQ ID NO:1) gene and all variations thereof, or any further transcripts which may be elucidated.

DESCRIPTION OF THE FIGURES

FIG. 1A-B sets forth the complete nucleotide sequence (SEQ ID NO:1) of STK-1 cDNA and the predicted amino acid sequence (SEQ ID NO:2). Amino acids are numbered to the left of each column and nucleotides to the right. FIG. 1A sets forth the first 1677 nucleotides of the STK-1 cDNA nucleotide sequence (SEQ ID NO:1, nucleotides 1–1677) and the corresponding first 521 amino acids of the predicted STK-1 amino acid sequence (SEQ ID NO:2, amino acids 1–521). Figure 1B sets forth the remaining 1800 nucleotides of the STK-1 cDNA nucleotide sequence (SEQ ID NO:1, nucleotides 1678–3477) and the corresponding remaining 460 amino acids of the predicted STK-1 amino acid sequence (SEQ ID NO:2, amino acids 522–981).

The predicted signal peptide, comprising a unique protein tyrosine kinase receptor sequence (amino acids 1–23), is underlined in FIG. 1A. The probable cleavage site that follows the signal peptide is marked with an arrow. The 22 cysteine residues of the extracellular domain of the STK-1 cDNA sequence are circled in FIGS. 1A and 1B. Also, in FIGS. 1A and 1B, the potential tripeptide asparagine-linked glycosylation sites are boxed. In Figure 1B, the single transmembrane spanning region is underlined (amino acids 542–562), as is the kinase insert region (amino acids 708–782) of the cytoplasmic domain. In Figure 1B, several of the conserved domains of protein tyrosine kinases (PTKs) including the GXGXXG (amino acids 617–622, ATP binding domain), DFG (amino acids 829–831), and WMAPES (amino acids 835–840) motifs in the cytoplasmic domain are boxed. The peptides which may be used to design degenerate oligonucleotides for a PCR amplification of the STK-1 cDNA are identified in Figure 1B by ovals (amino acids 808–813 and 870–875).

FIG. 4B is a histogram of the effect of STK-1 antisense oligonucleotides on normal hematopoietic cell colony growth in long-term bone marrow cultures (LTBMCs). CD34+ cells from long-term cultures were contacted with STK-1 oligomers at the indicated concentrations. After 36 hours of contact with the antisense oligomers, the CD34+ cells were assayed for colony-forming unit-granulocyte-erythroid-macrophage-megakaryocyte (CFU-GEMM) colonies.

DETAILED DESCRIPTION OF THE INVENTION

Figure 2:
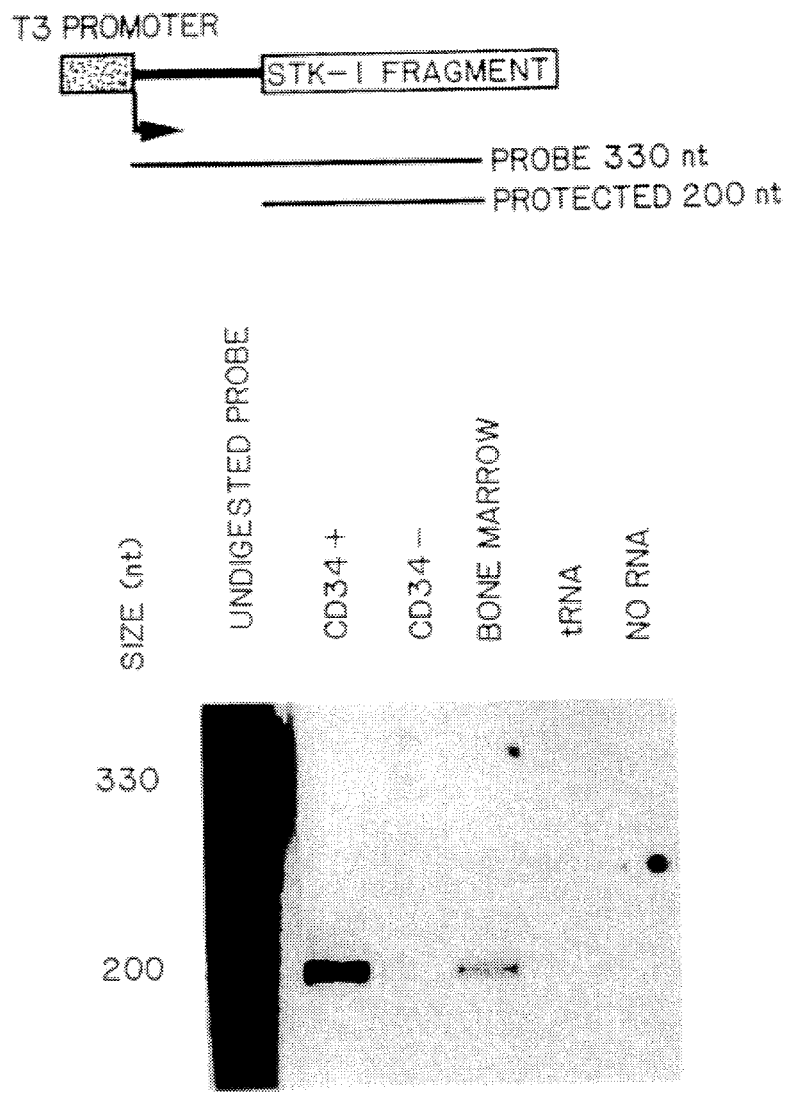
FIG. 2 is a comparison of STK-1 expression in bone marrow subpopulations by RNAse protection. The upper half of the figure is a schematic representation of the STK-1 bacteriophage promoter construct. Both the transcript size and predicted protected fragment size are indicated in the schematic. The lower half of the figure provides the blots illustrating the RNAse protection result. The first lane is a blot of the undigested probe. The second to sixth lanes are blots of the digested products after hybridization with equal quantities of RNA from CD34+, CD34−, total bone marrow cells, tRNA, or no RNA. The size markers are from a sequencing ladder run in the same electrophoresis gel.

The cDNA nucleotide sequence of the STK-1 gene and predicted 993 amino acid polypeptide are provided in SEQ ID NOS:1 and 2, respectively.

The STK-1 protein includes the following domains: (1) a hydrophobic leader sequence, (2) a hydrophilic extracellular domain, which binds to, and is activated by, a specific ligand, (3) a hydrophobic transmembrane region, and (4) a basic catalytic domain.

The first 57 nucleotides of the STK-1 gene cDNA comprise a 5' non-coding region. The initiation codon comprises nucleotides 58–60. The end-point of the STK-1 gene translation is at nucleotide 2976. After nucleotide 2976, the cDNA terminates with a 500 nucleotide 3' non-coding region (nucleotides 2977–3477).

The STK-1 gene encodes a receptor PTK which is expressed in proliferating hematopoietic stem cells but not quiescent stem cells. The STK-1 gene is also expressed in certain malignant cells of non-hematopoietic origin.

Disease conditions characterized by the expression of the STK-1 gene are, for example, (1) various hematologic neoplasms, such as disorders manifested by proliferation of immature hematopoietic stem cells, and (2) solid tumors, such as malignant melanoma, neuroectodermal cancers such as neuroblastoma and neuroepithelioma, breast cancer, prostate cancer, and mesothelial cancer. The leukemias and solid tumors characterized by STK-1 expression and believed treatable with STK-1 specific antisense oligonucleotide collectively represent tumors of endo-, ecto- and meso-thelial origin.

The antisense oligonucleotides of the invention are useful in the treatment of hematologic malignancies characterized by STK-1 expression. Malignant hematopoietic cells are characterized by an exponential growth phase. Inhibition of the STK-1 protein expression in such cells inhibits cell proliferation and leads to cell death. Hematologic disorders treatable with the antisense oligonucleotides of the invention include myeloproliferative disorders, including malignancies arising from immature progenitor blood cells.

While the antisense oligonucleotides of the invention may inhibit normal hematopoiesis to some extent, they are expected to inhibit the growth of malignant hematopoietic stem cells to a significantly greater extent. Quiescent hematopoietic cells do not express STK-1 and are therefore likely less sensitive to STK-1 antisense inhibition. Malignant cells are rapidly proliferating and express STK-1. This differential sensitivity between normal and malignant cells is expected to render the instant oligonucleotides useful in treating hematological neoplasms.

Hematopoietic malignancies believed sensitive to the STK-1 antisense oligonucleotides include, for example, myeloid and lymphatic leukemia cells, malignant plasma (myeloma) cells and lymphoma cells. Neoplasms of hematologic origin, occurring in the bone marrow and elsewhere in the body include all of the various French-American-British (FAB) subtype of acute myeloid (AML) and lymphatic leukemia; chronic lymphatic leukemia and chronic myeloid leukemia (CML); plasma cell myeloma and plasma cell dyscrasia; the various non-Hodgkin's lymphomas as described, for example, in the Working Formulation classification, Devita, *Cancer; Principals and Practice of Oncology* (2d ed. 1985), p.1634; and possibly Hodgkin's Disease.

The STK-1 antisense oligonucleotides of the invention inhibit proliferation of colony forming unit granulocyte-macrophage cells (CFU-GM), the progenitors of blood granulocytes. Hence, the oligonucleotides are believed useful in treating disorders characterized by aberrant myelopoiesis, i.e., myeloproliferative disorders. Such disorders are characterized by the proliferation, more or less et masse, of hematopoietic stem cells. The proliferation is self-perpetuating, resembling neoplastic disease.

Hematologic neoplastic cells, which are described above, would likely arise de novo in the marrow. In Hodgkin's Disease, and in some of the various lymphomas, tumor cells may metastasize to the marrow from a primary tumor situated elsewhere in the body.

Myeloproliferative disorders include, for example, chronic myeloid leukemia (CML), polycythemia vera, myelofibrosis with myeloid metaplasia, and essentially (Idiophathic) thrombocythemia. Presence of such cells in the bone marrow and elsewhere in the body is associated with various disease conditions, such as all of the subtypes of acute myeloid leukemia (AML); and chronic myeloid leukemia (CML).

CML, in particular, is characterized by abnormal proliferation of immature granulocyte—neutrophils, eosinophils, and basophils—in the blood, the bone marrow, the spleen, the liver, and sometimes other tissues. The essential feature is accumulation of granulocytic precursors in these tissues. The patient who presents symptoms will characteristically have more than 20,000 white blood cells per μl, and the count may exceed 400,000. Virtually all CML patients will develop "blast crisis", the terminal stage of the disease during which immature blast cells rapidly proliferate, leading to patient death.

Malignant myeloid cell colony formation is sensitive to inhibition by the STK-1 antisense oligonucleotides. This sensitivity makes possible the use of STK-1 antisense oligonucleotides as antileukemic agents, in particular, in purging neoplastic cells from bone marrow.

In addition to hematologic neoplasms, antisense oligonucleotides of the invention are useful in the treatment of neoplastic diseases of non-hematopoietic origin, i.e., solid tumors, which express STK-1. These disorders include neoplastic diseases wherein proliferation of the neoplastic cell is controlled at least in part by STK-1 expression. Neoplastic diseases characterized by cells expressing STK-1 include, for example, malignant melanona, neuroectodermal cancers, breast cancer, prostate cancer and mesothelioma. STK-1 expression is signaled by the appearance of STK-1 mRNA transcripts, and/or the appearance of the 981 amino acid protein product.

Melanoma, also known as "malignant melanoma" or "cutaneous melanoma", is a neoplasm of a melanocyte that has the potential for invasion and metastasis. Melanocytes are melanosome-containing cells that specialize in the biosynthesis and transport of melanin pigment. Melanocytes reside in the skin at the basal layer of the epidermis. Under a variety of stimuli, they elaborate melanin pigment. Melanin synthesis occurs on the melanosome, a well-defined intracellular organelle within the melanosome.

At one time considered rare, the rate of increase in the incidence of melanoma is greater than for any other cancer, with the exception of bronchogenic carcinoma. The incidence of melanoma is greatest among Caucasians, and is influenced by ultraviolet light exposure, and by geographical and occupational factors. The incidence of melanoma is increasing rapidly in the United States and elsewhere, with an apparent doubling every ten to seventeen years. Presently, melanoma accounts for roughly one percent of cancers in the United States, and about the same proportion of cancer deaths. While it represents only about three percent of cutaneous neoplasms, melanoma accounts for two thirds of all skin cancer fatalities.

For the most part, melanoma first progresses through a radial growth phase at the site of the primary lesion. This initial phase is characterized by little or no competence to metastasize. Melanomas in this phase are generally treatable by surgical procedures. In the vertical growth phase, characterized by penetration into deeper cutaneous tissues, a primary melanoma acquires competence to metastasize. Surgery alone is ineffective in treating the melanoma, once metastasis has occurred.

Tumors of neuroectodermal original include neuroblastoma and neuroepithelioma tumors. Neuroblastoma is a tumor of the peripheral nervous system and is thought to arise in cells of the embryonal neural crest. Neuroblastoma is histopathologically indistinguishable from neuroepithelioma. The two malignancies are often considered as one entity.

Neuroblastoma is the most common extracranial malignant solid tumor in childhood with an occurrence of 10 per million children annually. It accounts for 8% of all pediatric tumors and causes 11% of all deaths from cancer in children. It arises in the adrenal medulla and/or sympathetic ganglia, spreading as a disseminated disease. Neuroblastoma is characterized by a fairly high degree of spontaneous regression. Neuroblastoma cells can be induced to differentiate in vitro by various chemicals and biological response modifiers.

Neuroblastoma mainly occurs in early childhood. Clinically, patients are divided roughly into two groups: (i) those with good prognosis having a localized tumor (stages I and II), or stage IV very young infants with a small primary tumor and metastasis mainly to liver and/or skin and marrow, and (ii) patients with a very poor prognosis, that is, patients over one year of age with a very poor prognosis, having unrespectable or metastasized tumors (stages III and IV).

Neoplasms of the prostate are common in older men. About 95% of the prostatic carcinomas arise in the glandular epithelium of the peripheral glands of the prostate. Prostate neoplasms include soft tumors of the endothelium (soft-tissue cancer).

Neoplasms of the human breast include soft-tissue cancer of the breast epithelium. In North America, breast cancer is the most common malignancy among women and accounts for 27% of their cancers. Older women have a greater instance of breast cancer. The most common breast cancer is an invasive (infiltrating) carcinoma of the breast. These endothelial ductal tumors account for almost 70% of breast cancers.

Malignant mesothelioma is another neoplasm which expresses STK-1. It is strongly associated with the widely distributed environmental carcinogen, asbestos. Malignant mesothelioma is manifested as a lung cancer. An increased incidence of mesothelioma is detectable in a population about 15 years after first asbestos exposure and rises steadily to 5.5 per 1,000 person-years 40–45 years after first exposure. Despite legislation limiting industrial exposure to asbestos since 1970, an estimated 19,000 to 80,000 new cases of asbestosis-associated mesothelioma have been expected to occur between 1980 and 2030. Because mesotheliomas develop in tissues of mesodermal embryologic origin, they are generally classified as soft tissue sarcomas. After a median of 6 to 18 months in various series, (range weeks to 16 years), patients die, usually of a respiratory problem.

Cells may be assayed for expression of the STK-1 gene, and hence likely sensitivity to growth inhibition by a STK-1 antisense oligonucleotide, by conventional probing techniques, such as described by Lammie et al., *Oncogene* 6, 439–444 (1991). The level of STK-1 expression is determined by probing total cellular RNA from a potential target cell with a nucleotide probe complementary to a portion of STK-1 mRNA. Total RNA from the cells to be assayed is fractionated in a glyoxal/agarose gel, transferred to nylon and hybridized to an appropriately labeled nucleic acid probe specific for STK-1 mRNA. See Lammie, et al., supra. The presence of STK-1 mRNA transcripts found in the assayed cell is an indication that the STK-1 gene is expressed by the assayed cell. Alternatively, the total cellular RNA is assayed for STK-1 mRNA by reverse transcribing the RNA transcript (RT) and amplifying a portion of the resulted cDNA by a polymerase chain reaction (PCR) (RT-PCR). A RT-PCR procedure as applied to the determination of STK-1 expression in cells is illustrated in Example 2A, below.

Alternatively, the expression of STK-1 may be assayed by Western blot analysis. After total protein has been isolated from the hematopoietic or tumor cell to be assayed, the protein is electrophoresed and probed with a polyclonal or monoclonal antibody specific for the STK-1 protein. A Western blot analysis for STK-1 expression by cells is illustrated in Example 3 and in FIGS. 3A and 3B.

Antisense oligonucleotides specific for a portion of the DNA or mRNA sequence coding for STK-1 display toxicity towards leukemias and solid tumor cell types which express the STK-1 protein. Neoplastic cells, by virtue of their rapid proliferation, are believed more susceptible to STK-1 antisense oligonucleotides than normal cells.

In particular, tumor cells which overexpress STK-1 are believed sensitive to inhibition by STK-1 antisense oligonucleotides. A cell is "overexpressing" STK-1 if its level of STK-1 expression is at least several times higher than that of the level of expression characteristic of normal STK-1-expressing cells, such as normal hematopoietic stem cells. STK-1 expression levels in leukemic cells may be compared to the expression level in normal hematopoietic stem cells. STK-1 overexpression in the former, as compared to the latter, is an indication that the tested cells may be sensitive to growth inhibition by STK-1 antisense oligonucleotides.

We assayed various hematologic neoplasms for their level of STK-1 expression. All expressed STK-1 at a level which was at least equal to normal stem cells. Cells from several leukemia patients significantly over-expressed STK-1. Overexpression levels ranged from several-fold to several hundred-fold the level of STK-1 expression in normal hematopoietic stem cells. For example, cells from twenty out of twenty-two patients with AML overexpressed STK-1. B-lineage cells from twenty-four out of twenty-four acute lymphocytic (ALL) leukemia overexpressed STK-1. Leukemic T-cells from three out of nine ALL patients overexpressed STK-1. However, cells from patients with CML did not overexpress STK-1.

The target polynucleotide against which the STK-1 antisense oligonucleotide is directed may be single-stranded or double-stranded DNA or RNA segment, but, single-stranded DNA or RNA targets are preferred. It is understood that the target to which the STK-1 antisense oligonucleotides of the invention are directed include allelic forms of the STK-1 gene. For further 10 guidance in the literature for selecting additional sequences for antisense oligonucleotides, see e.g., e.g., Penman and Ulmann, *Chemical Reviews*, 90:543–584, 1990; Crooke, *Ann. Rev. Pharmacal. Toxicol.*, 32:329–376 (1992); and Zamecnik and Stephenson, *Proc. Natl. Acad. Sci.*, 75:280–284 (1974). Preferably, the sequences of STK-1 antisense compounds are selected such that the G-C content is at least 60%. Preferred gene mRNA targets include the 5' cap site, tRNA primer binding site, the mRNA donor splice site, and the mRNA acceptor splice site, e.g., Goodchild et al., U.S. Pat. No. 4,806,463.

Where the target polynucleotide comprises the STK-1 mRNA transcript, oligonucleotides complementary to and hybridizable with any portion of the transcript are, in principle, effective for inhibiting translation, and capable of inducing the effects herein described. It is believed that translation is most effectively inhibited by blocking the mRNA in the 5'-region of the STK-1 mRNA transcript are preferred. Oligonucleotides complementary to the STK-1 mRNA, in the 5' non-coding region of the STK-1 transcript are preferred.

Antisense oligomers complementary to the 5'-region of the STK-1 mRNA transcript are preferred. However, it should be appreciated that useful antisense oligomers are not limited to those complementary to the sequences found in the translated portion of the mRNA transcript. Also included are oligomers complementary to nucleotide sequences contained in, or extending into, the 5'- and 3'-untranslated regions.

A preferred 50-mer oligodeoxynucleotide is complementary to the STK-1 mRNA transcript beginning with the first nucleotide of SEQ ID NO:1 and extending 50 nucleotides downstream thereof. Another preferred 50-mer oligonucleotide is complemented to the STK-1 mRNA transcript beginning with nucleotide 121 and extending 50 nucleotides downstream thereof. Smaller oligomers based upon the above sequence may be utilized. Particularly preferred are oligomers containing at least 12 nucleotides, having a nucleotide sequence complementary to a portion of nucleotides 1–57 and 121–148 of SEQ ID NO:1.

In principle oligonucleotides having a sequence complementary to any region of the STK-1 mRNA find utility in the present invention. Preferred oligonucleotides are capable of forming a stable duplex with a portion of the STK-1 transcript.

Antisense oligonucleotides of the invention may comprise any polymeric compound capable of specifically binding to a target polynucleotide by way of a regular pattern of monomer-to-nucleoside interactions, such as Watson-Crick type of base pairing, Hoogsteen or reverse Hoogsteen types of base pairing, or the like. Antisense compounds of the invention may also contain pendent groups or moieties, either as part of or separate from the basic repeat unit of the polymer, to enhance specificity, nuclease resistance, delivery, or other property related to efficacy, e.g., cholesterol moieties, duplex intercalators such as acridine, poly-L-lysine, "end-capping" with one or more nuclease-resistant linkage groups such as phosphorothioate, and the like.

For example, it is known that enhanced lipid solubility and/or resistance to nuclease digestion results by substituting an alkyl group or alkoxy group for a phosphate oxygen in the internucleotide phosphodiester linkage to form an alkylphosphonate oligonucleoside or alkylphosphotriester oligonucleotide. Non-ionic oligonucleotides such as these are characterized by increased resistance to nuclease hydrolysis and/or increased cellular uptake, while retaining the ability to form stable complexes with complementary nucleic acid sequences. The alkylphosphonates, in particular, are stable to nuclease cleavage and soluble in lipid. The preparation of alkylphosphonate oligonucleotides is disclosed in Tso et al., U.S. Pat No. 4,469,863.

Preferably, nuclease resistance is conferred on the antisense compounds of the invention by providing nuclease-resistant internucleosidic linkages. Many such linkages are known in the art, e.g., phosphorothioate: Zon and Geiser, *Anti-Cancer Drug Design*, 6:539–568 (1991); Stec et al., U.S. Pat No. 5,151,510; Hirschbein, U.S. Pat No. 5,166,387; Bergot, U.S. Pat No. 5,183,885; phosphorodithioates: Marshall et al., Science, 259:1564–1570 (1993); Caruthers and Nielsen, International application PCT/US89/02293; phosphoramidates, e.g., —OP(=O)—(NR$^1$R$^2$)—O— with R$^1$ and R$^2$ hydrogen or $C_{1-C3}$ alkyl; Jager et al., *Biochemistry*, 27:7237–7246 (1988); Froehler et al., International application PCT/US90/03138; peptide nucleic acids: Nielsen et al., *Anti-Cancer Drug Design*, 8:53–63 (1993), International application PCT/EP-92/01220; methylphosphonates: Miller et al., U.S. Pat. No. 4,507,433, Ts'o et al., U.S. Pat No.4, 469,863; Miller et al., U.S. Pat No.4,757,055; and P-chiral linkages of various types, especially phosphorothioates, Stec et al., European patent application 506,242 (1992) and Lesnikowski, *Bioorganic Chemistry*, 21:127–155 (1993). Additional nuclease linkages include phosphoroselenoate, phosphorodiselenoate, phosphoroanilothioate, phosphoranilidate, alkylphosphotriester such as methyl- and ethylphosphotriester, carbonate such as carboxymethyl ester, carbamate, morpholino carbamate, 3'-thioformacetal, silyl such as dialkyl($C_1$–$C_6$) - or diphenylsilyl, sulfamate ester, and the like. Such linkages and methods for introducing them into oligonucleotides are described in many references, e.g., reviewed generally by Peyman and Ulmann, *Chemical Reviews* 90:543–584 (1990); Milligan et al., *J. Med. Chem.*, 36:1923–1937 (1993); Matteucci et al., International application PCT/US91/06855.

Resistance to nuclease digestion may also be achieved by modifying the internucleotide linkage at both the 5' and 3' termini with phosphoroamidites according to the procedure of Dagle et al., *Nucl. Acids Res.* 18, 4751–4757 (1990).

Preferably, phosphorus analogs of the phosphodiester linkage are employed in the compounds of the invention, such as phosphorothioate, phosphorodithioate, phosphoramidate, or methylphosphonate. More preferably, phosphorothioate is employed as the nuclease resistant linkage.

Phosphorothioate oligonucleotides contain a sulfur-for-oxygen substitution in the internucleotide phosphodiester bond. Phosphorothioate oligonucleotides combine the properties of effective hybridization for duplex formation with substantial nuclease resistance, while retaining the water solubility of a charged phosphate analogue. The charge is believed to confer the property of cellular uptake via a receptor (Loke et al., *Proc. Natl. Acad. Sci.*, 86, 3474–3478 (1989)).

It is understood that in addition to the preferred linkage groups, compounds of the invention may comprise additional modifications, e.g., boronated bases Spielvogel et al., 5,130,302; cholesterol moieties, Shea et al., *Nucleic Acids Research*, 18:3777–3783 (1990) or Letsinger et al., *Proc. Natl. Acad. Sci.*, 86:6553–6556 (1989); and 5-propynyl modification of pyrimidines, Froehler et al., *Tetrahedron Lett.*, 33:5307–5310 (1992).

Preferably, antisense compounds of the invention are synthesized by conventional means on commercially available automated DNA synthesizers, e.g., an Applied Biosystems (Foster City, Calif.) model 380B, 392 or 394 DNA/RNA synthesizer. Preferably, phosphoramidite chemistry is employed, e.g., as disclosed in the following references: Beaucage and Iyer, *Tetrahedron*, 48 2223–2311 (1992); Molko et al., U.S. Pat No. 4,980,460; Koster et al., U.S. Pat No. 4,725,677; Caruthers et al., U.S. Pat Nos. 4,415,732; 4,458,066; and 4,973,679.

In embodiments where triplex formation is desired, there are constraints on the selection of target sequences. Generally, third strand association via Hoogsteen type of binding is most stable along homopyrimidine-homopurine tracks in a double stranded target. Usually, base triplets form in T-A*T or C-G*C motifs (where "-" indicates Watson-Crick pairing and "*" indicates Hoogsteen type of binding); however, other motifs are also possible. For example, Hoogsteen base pairing permits parallel and antiparallel orientations between the third strand (the Hoogsteen strand) and the purinerich strand of the duplex to which the third strand binds, depending on conditions and the composition of the strands. There is extensive guidance in the literature for selecting appropriate sequences, orientation, conditions, nucleoside type (e.g., whether ribose or deoxyribose nucleosides are employed), base modifications (e.g., methylated cytosine, and the like) in order to maximize, or otherwise regulate, triplex stability as desired in particular embodiments, e.g., Roberts et al., *Proc. Natl. Acad. Sci.*, 88:9397–9401 (1991); Roberts et al., *Science*, 258:1463–1466 (1992); Distefano et al., *Proc. Natl. Acad. Sci.*, 90:1179–1183 (1993); Mergny et al., *Biochemistry*, 30:9791–9798 (1992); Cheng et al., *J. Am. Chem. Soc.*, 114:4465–4474 (1992); Beal and Dervan, *Nucleic Acids Research*, 20:2773–2776 (1992); Beal and Dervan, *J. Am. Chem. Soc.*, 114:4976–4982; Giovannangeli et al., *Proc. Natl. Acad. Sci.*, 89:8631–8635 (1992); Moser and Dervan, *Science*, 238:645–650 (1987); McShan et al., *J. Biol. Chem.*, 267:5712–5721 (1992); Yoon et al., *Proc. Natl. Acad. Sci.*, 89:3840–3844 (1992); and Blume et al., *Nucleic Acids Research*, 20:1777–1784 (1992).

The length of the oligonucleotide moieties is sufficiently large to ensure that specific binding will take place only at the desired target polynucleotide and not at other fortuitous sites, as explained in many references, e.g., Rosenberg et al., International application PCT/US92/05305; or Szostak et al., *Meth. Enzymol*, 68:419–429 (1979). According to one embodiment, the antisense oligonucleotide has a nucleotide sequence capable of forming a stable duplex with a portion of a mRNA transcript gene. Generally, the antisense oligonucleotide is at least an 8-mer oligomer. That is, the oligonucleotide contains at least 8 nucleotide residues, more preferably at least about 12 nucleotides. Antisense oligonucleotides that are specific for STK-1, which are smaller than 12-mers may be utilized. However, oligonucleotides smaller than 12-mers are statistically more likely to hybridize with non-targeted sequences, and for this reason may be less specific. In addition, a single mismatch may stabilize the hybrid. The upper range of the length is determined by several factors, including the inconvenience and expense of synthesizing and purifying oligomers greater than about 30–40 nucleotides in length. Also, there is a greater tolerance of longer oligonucleotides for mismatches than shorter oligonucleotides. Partial matching of long sequences may lead to non-specific hybridization, and nonspecific effects. Other factors affecting the maximum length are whether modifications to enhance binding or specificity are present, whether duplex or triplex binding is desired, and the like. While oligonucleotides larger than 40-mers may be utilized, uptake may become more difficult without specialized vehicles or oligonucleotide carriers. The preferred maximum size of the oligonucleotide is about 60 nucleotides, more preferably about 50 nucleotides. Most preferably, the oligonucleotide is a 15- to 40-mer oligodeoxynucleotide, more advantageously an 18- to 30-mer. The oligomer is preferably an oligodeoxynucleotide.

In general, the antisense oligonucleotides used in the practice of the present invention will have a sequence which is completely complementary to a selected portion of the target polynucleotide. Absolute complementarity is not however required, particularly in larger oligomers. Thus, reference herein to a "nucleotide sequence complementary to" a target polynucleotide does not necessarily mean a sequence having 100% complementarity with the target segment. In general, any oligonucleotide having sufficient complementarity to form a stable duplex with the target (e.g. the STK-1 mRNA) that is, an oligonucleotide which is "hybridizable", is suitable. Stable duplex formation depends on the sequence and length of the hybridizing oligonucleotide and the degree of complementarity with the target polynucleotide. Generally, the larger the hybridizing oligomer, the more mismatches may be tolerated. More than one mismatch probably will not be tolerated for antisense oligomers of less than about 21 nucleotides. One skilled in the art may readily determine the degree of mismatching which may be tolerated between any given antisense oligomer and the target sequence, based upon the melting point, and therefore the thermal stability, of the resulting duplex.

Preferably, the thermal stability of hybrids formed by the antisense oligonucleotides of the invention are determined by way of melting, or strand dissociation, curves. The temperature of fifty percent strand dissociation is taken as the melting temperature, $T_m$, which, in turn, provides a convenient measure of stability. $T_m$ measurements are typically carried out in a saline solution at neutral pH with target and antisense oligonucleotide concentrations at between about 1.0–2.0 µM. Typical conditions are as follows:150 mM NaCl and 10 mM $MgCl_2$ in a 10 mM sodium phosphate buffer (pH 7.0) or in a 10 mM Tris-HCl buffer (pH 7.0). Data for melting curves are accumulated by heating a sample of the antisense oligonucleotide/target polynucleotide complex from room temperature to about 85°–90° C. As the temperature of the sample increases, absorbance of 260 nm light is monitored at 1° C. intervals, e.g., using a Cary (Australia) model 1E or a Hewlett-Packard (Palo Alto, Calif.) model HP 8459 UV/VIS spectrophotometer and model HP 89100A temperature controller, or like instruments. Such techniques provide a convenient means for measuring and comparing the binding strengths of antisense oligonucleotides of different lengths and compositions.

Pharmaceutical compositions of the invention include a pharmaceutical carrier that may contain a variety of components that provide a variety of functions, including regulation of drug concentration, regulation of solubility, chemical stabilization, regulation of viscosity, absorption enhancement, regulation of pH, and the like. The pharmaceutical carrier may comprise a suitable liquid vehicle or excipient and an optional auxiliary additive or additives. The liquid vehicles and excipients are conventional and commercially available. Illustrative thereof are distilled water, physiological saline, aqueous solutions of dextrose, and the like. For water soluble formulations, the pharmaceutical composition preferably includes a buffer such as a phosphate buffer, or other organic acid salt, preferably at a pH of between about 7 and 8. For formulations containing weakly soluble antisense compounds, microemulsions may be employed, for example by using a nonionic surfactant such as polysorbate 80 in an amount of 0.04–0.05% (w/v), to increase solubility. Other components may include antioxidants, such as ascorbic acid, hydrophilic polymers, such as, monosaccharides, disaccharides, and other carbohydrates including cellulose or its derivatives, dextrines, chelating agents, such as EDTA, and like components well known to those in the pharmaceutical sciences, e.g., *Remington's Pharmaceutical Science*, latest edition (Mack Publishing Company, Easton, Pa).

Antisense compounds of the invention include the pharmaceutically acceptable salts thereof, including those of alkaline earths, e.g., sodium or magnesium, ammonium or $NX_4^+$, wherein X is $C_1$–$C_4$ alkyl. Other pharmaceutically acceptable salts include organic carboxylic acids such as acetic, lactic, tartaric, malic, isethionic, lactobionic, and succinic acids; organic sulfonic acids such as methanesulfonic, ethanesulfonic, and benzenesulfonic; and inorganic acids such as hydrochloric, sulfuric, phosphoric, and sulfamic acids. Pharmaceutically acceptable salts of a compound having a hydroxyl group include the anion of such compound in combination with a suitable cation such as $Na^+$, $NH_4^+$, or the like.

The STK-1 antisense oligonucleotides are preferably administered parenterally, most preferably intravenously.

The vehicle is designed accordingly. Alternatively, oligonucleotide may be administered subcutaneously via controlled release dosage forms.

In addition to administration with conventional carriers, the antisense oligonucleotides may be administered by a variety of specialized oligonucleotide delivery techniques. Sustained release systems suitable for use with the pharmaceutical compositions of the invention include semi-permeable polymer matrices in the form of films, microcapsules, or the like, comprising polylactides, copolymers of L-glutamic acid and gammaethyl-L-glutamate, poly(2-hydroxyethyl methacrylate), and like materials, e.g., Rosenberg et al., International application PCT/US92/05305.

The oligonucleotides may be encapsulated in liposomes for therapeutic delivery, as described for example in *Liposome Technology*, Vol. II, *Incorporation of Drugs, Proteins, and Genetic Material*, CRC Press. The oligonucleotide, depending upon its solubility, may be present both in the aqueous layer and in the lipidic layer, or in what is generally termed a liposomic suspension. The hydrophobic layer, generally but not exclusively, comprises phospholipids such as lecithin and sphingomyelin, steroids such as cholesterol, ionic surfactants such as diacetylphosphate, stearylamine, or phosphatidic acid, and/or other materials of a hydrophobic nature.

The oligonucleotides may be conjugated to poly(L-lysine) to increase cell penetration. Such conjugates are described by Lemaitre et al., *Proc. Natl. Acad. Sci. USA*, 84, 648–652 (1987). The procedure requires that the 3'-terminal nucleotide be a ribonucleotide. The resulting aldehyde groups are then randomly coupled to the epsilon-amino groups of lysine residues of poly(L-lysine) by Schiff base formation, and then reduced with sodium cyanoborohydride. This procedure converts the 3'-terminal ribose ring into a morpholine structure antisense oligomers.

Antisense compounds of the invention also include conjugates of such oligonucleotides with appropriate ligand-binding molecules. The oligonucleotides may be conjugated for therapeutic administration to ligand-binding molecules which recognize cell-surface molecules, such as according to International Patent Application WO 91/04753. The ligand-binding molecule may comprise, for example, an antibody against a cell surface antigen, an antibody against a cell surface receptor, a growth factor having a corresponding cell surface receptor, an antibody to such a growth factor, or an antibody which recognizes a complex of a growth factor and its receptor. Methods for conjugating ligand-binding molecules to oligonucleotides are detailed in WO 91/04753.

In particular, the growth factor to which the antisense oligonucleotide may be conjugated, may comprise transferrin or folate. Transferrin-polylysineoligonucleotide complexes or folate-polylysine-oligonucleotide complexes may be prepared for uptake by cells expressing high levels of transferrin or folate receptor. The preparation of transferrin complexes as carriers of oligonucleotide uptake into cells is described by Wagner et al., *Proc. Natl. Acad. Sci. USA* 87, 3410–3414 (1990). Inhibition of leukemia cell proliferation by transferrin receptor-mediated uptake of c-myb antisense oligonucleotides conjugated to transferrin has been demonstrated by Citro et al., *Proc. Natl. Acad. Sci. USA.*, 89, 7031–7035 (1992). Cellular delivery of folate-macromolecule conjugates via folate receptor endocytosis, including delivery of an antisense oligonucleotide, is described by Low et al., U.S. Pat. No. 5,108,921. Also see, Leamon et al., *Proc. Natl. Acad. Sci.* 88, 5572 (1991).

A preferred method of administration of oligonucleotide comprises either systemic or regional perfusion, as is appropriate. According to a method of regional perfusion, the afferent and efferent vessels supplying the extremity containing the lesion are isolated and connected to a low-flow perfusion pump in continuity with an oxygenator and a heat exchanger. The iliac vessels may be used for perfusion of the lower extremity. The axillary vessels are cannulated high in the axilla for upper extremity lesions. Oligonucleotide is added to the perfusion circuit, and the perfusion is continued for an appropriate time period, e.g., one hour. Perfusion rates of from 100 to 150 ml/minute may be employed for lower extremity lesions, while half that rate should be employed for upper extremity lesions. Systemic heparinization may be used throughout the perfusion, and reversed after the perfusion is complete. This isolation perfusion technique permits administration of higher doses of chemotherapeutic agent than would otherwise be tolerated upon infusion into the arterial or venous systemic circulation.

For systemic infusion, the oligonucleotides are preferably delivered via a central venous catheter, which is connected to an appropriate continuous infusion device. Indwelling catheters provide long term access to the intravenous circulation for frequent administration of drugs over extended time periods. They are generally surgically inserted into the external cephalic or internal jugular vein under general or local anesthesia. The subclavian vein is another common site of catheterization. The infuser pump may be external, or may form part of an entirely implantable central venous system such as the INFUSAPORT system available from Infusaid Corp., Norwood, MA and the PORT-A-CATH system available from Pharmacia Laboratories, Piscataway, N. J. These devices are implanted into a subcutaneous pocket under local anesthesia. A catheter, connected to the pump injection port, is threaded through the subclavian vein to the superior vena cava. The implant contains a supply of oligonucleotide in a reservoir which may be replenished as needed by injection of additional drug from a hypodermic needle through a self-sealing diaphragm in the reservoir. Completely implantable infusers are preferred, as they are generally well accepted by patients because of the convenience, ease of maintenance and cosmetic advantage of such devices.

As an alternative to treatment with exogenous oligonucleotide, antisense oligonucleotide synthesis may be induced in situ by local treatment of the targeted neoplastic cells with a vector containing an artificially-constructed gene comprising a transcriptional promoter and STK-1 DNA in inverted orientation. The STK-1 DNA for insertion into the artificial gene in inverted orientation comprises cDNA which may be prepared, for example, by reverse transcriptase polymerase chain reaction from RNA using primers derived from the cDNA sequence according to SEQ ID NO:1. Upon transcription, the inverted STK-1 gene segment, which is complementary to the STK-1 mRNA, is produced in situ in the targeted cell. The endogenously produced RNA hybridizes to STK-1 mRNA, resulting in interference with STK-1 function and inhibition of the proliferation of the targeted cell.

The promotor segment of the artificially-constructed gene serves as a signal conferring expression of the inverted STK-1 sequence which lies downstream thereof. It will include all of the signals necessary for initiating transcription of the sequence. The promoter may be of any origin as long as it specifies a rate of transcription which will produce sufficient antisense mRNA to inhibit the expression of the STK-1 gene, and therefore the proliferation of the targeted malignant cells. Preferably, a highly efficient promotor such as a viral promoter is employed. Other sources of potent promoters include cellular genes that are expressed at high levels. The promotor segment may comprise a constitutive or a regulatable promotor.

The artificial gene may be introduced by any of the methods described in U.S. Pat. No. 4,740,463, incorporated herein by reference. One technique is transfection, which can be done by several different methods. One method of transfection involves the addition of DEAE-dextran to increase the uptake of the naked DNA molecules by a recipient cell. See McCutchin, J.H. and Pagano, J.S., *J. Natl. Cancer Inst.* 41, 351–7 (1968). Another method of transfection is the calcium phosphate precipitation technique which depends upon the addition of $Ca^{++}$ to a phosphate-containing DNA solution. The resulting precipitate apparently includes DNA in association with calcium phosphate crystals. These crystals settle onto a cell monolayer; the resulting apposition of crystals and cell surface appears to lead to uptake of the DNA. A small proportion of the DNA taken up becomes expressed in a transfectant, as well as in its clonal descendants. See Graham, F.L. and van der Eb, A.J., *Virology* 52, 456–467 (1973) and *Virology* 54, 536–539 (1973).

Transfection may also be carried out by cationic phospholipid-mediated delivery. In particular, polycationic liposomes can be formed from N-[1-(2,3dioleyloxy)propyl]-N,N,N-trimethylammonium chloride (DOTMA). See Felgner et al., *Proc. Natl. Acad. Sci.*, 84, 7413–7417 (1987) (DNA-transfection); Malone et al., *Proc. Natl. Acad. Sci.*, 86, 6077–6081 (1989) (RNA transfection).

Alternatively, the artificially-constructed gene can be introduced in to cells, in vitro or in vivo, via a transducing viral vector. See Tabin et al., *Mol. Cel. Biol.* 2,426–436 (1982). Use of a retrovirus, for example, will infect a variety of cells and cause the artificial gene to be inserted into the genome of infected cells. Such infection could either be accomplished with the aid of a helper retrovirus, which would allow the virus to spread through the organism, or the antisense retrovirus could be produced in a helper-free system, such as ψ2-like cells (See Mann et al., *Cell* 33, 153–160, 1983) that package amphotropic viruses. A helper-free virus might be employed to minimize spread throughout the organism. Viral vectors in addition to retroviruses can also be employed, such as papovaviruses, SV40-like viruses, or papilloma viruses. The use of retroviruses for gene transfer has been reviewed by Eglitis and Anderson, *BioTechniques* 6,608–614 (1988).

Vesicle fusion could also be employed to deliver the artificial gene. Vesicle fusion may be physically targeted to the malignant cells if the vesicle were approximately designed to be taken up by those cells. Such a delivery system would be expected to have a lower efficiency of integration and expression of the artificial gene delivered, but would have a higher specificity than a retroviral vector. A combination strategy of targeted vesicles containing papilloma virus or retrovirus DNA molecules might provide a method for increasing the efficiency of expression of targeted molecules.

Particulate systems and polymers for in vitro and in vivo delivery of polynucleotide were extensively reviewed by Felgner in *Advanced Drug Delivery Reviews* 5, 163–187 (1990). Techniques for direct delivery of purified genes in vivo, without the use of retroviruses, has been reviewed by Felgner in *Nature* 349, 351–352 (1991). Such methods of direct delivery of polynucleotide may be utilized for local delivery of either exogenous STK-1 antisense oligonucleotide or artificially-constructed genes producing STK-1 antisense oligonucleotide in situ.

Recently, Wolf et al. demonstrated that direct injection of non-replicating gene sequences in a nonviral vehicle is possible. See *Science*, 247, 1465–1468 (1990). DNA injected directly into mouse muscle did not integrate into the host genome, and plasmid essentially identical to the starting material was recovered from the muscle months after injection. Interestingly, no special delivery system is required. Simple saline or sucrose solutions are sufficient to delivery DNA and RNA.

The STK-1 antisense oligonucleotide may be administered to the patient either systemically, regionally or locally. Alternatively, the antisense oligonucleotides may be administered ex vivo, to cells harvested from the patient. Thus, according to an embodiment of the invention, the STK-1 antisense oligonucleotides are utilized as bone marrow purging agents for in vitro cleansing of the patient's bone marrow contaminated by leukemic cells, or neoplastic cells of other malignancies which have metastisized to the bone marrow. The antisense oligonucleotides are believed useful as purging agents in either allogeneic or autologous bone marrow transplation.

Many neoplasms, such as neurobiastoma, melanmoma and breast cancer, may be substantially metastic, particularly in advances stages. In particular, malignant cells may metastasize to the bone marrow. Patients with disseminated disease may have bone marrow metastases. It is therefore necessary to develop an effective method to purge bone marrow of all remaining neoplastic cells if autologous bone marrow transplatation is used in conjunction with aggressive chemotherapy. According to the present invention, STK-1 antisense oligonucleotides may be used as bone marrow purging agents for the in vitro cleansing of bone marrow of malignant cells which have mestastasized to the bone marrow from other tissues.

Bone marrow is aspirated from a patient suffering from a hematologic neoplasm, or a solid tumor which has metastasized to the bone marrow inflicted individual is treated with an effective amount of an STK-1 antisense oligonucleotide, and the thus-treated cells are then returned to the body of the afflicted individual. The bone marrow purging technique may be utilized for an autologous bone marrow rescue (transplantation), in connection with a course of high dose chemotherapy. High dose chemotherapy coupled with autologous bone marrow rescue involves removing a portion of the patient's bone marrow, treating the patient with conventional chemotherapy or radiation to substantially destroy the remaining malignant bone marrow cells, treating the stored bone marrow with a STK-1 antisense oligonucleotide, and returning the treated cells to the patient. The treated cells, when returned to the patient, may be stimulated by various known hematopoietic growth factors to repopulate the bone marrow with cells which do not carry the oncogenic transcript.

According to a method for bone marrow purging, bone marrow is harvested from a donor by standard operating room procedures from the iliac bones of the donor. Methods of aspirating bone marrow from donors are well-known in the art. Examples of apparatus and processes for aspirating bone marrow from donors are disclosed in U.S. Pat. Nos. 4,481,946 and 4,486,188. Sufficient marrow is withdrawn so that the recipient, who is either the donor (autologous transplant) or another individual (allogeneic transplant), may receive from about $4\times10^8$ to about $8\times10^8$ processed marrow cells per kg of bodyweight. This generally requires aspiration of about 750 to about 1000 ml of marrow. The aspirated marrow is filtered until a single cell suspension, known to those skilled in the art as a "buffy coat" preparation, is obtained. This suspension of leukocytes is treated with STK-1 antisense oligonucleotides in a suitable carrier, advantageously in a concentration of about 50–200 µg/ml. Alternatively, the leucocyte suspension may be stored in liquid nitrogen using standard procedures known to those skilled in the art until purging is carried out. The purged marrow can be stored frozen in liquid nitrogen until ready for use. Methods of freezing bone marrow and biological substances are disclosed, for example, in U.S. Pat. Nos. 4,107,937 and 4,117,881.

Other methods of preparing bone marrow for treatment with STK-1 antisense may be utilized, which methods may result in even more purified preparations of hematopoietic cells than the aforesaid buffy coat preparation.

One or more hematopoietic growth factors may be added to the aspirated marrow or buffy coat preparation to stimulate growth of hematopoietic neoplasms, and thereby increase their sensitivity to the toxicity of the antisense oligonucleotide. Such hematopoietic growth factors include, for example, IL-3 and granulocyte macrophage colony stimulating factor (GM-CSF). The recombinant human versions of such growth factors are advantageously employed.

After treatment with the antisense oligonucleotides, the cells to be transferred are washed with autologous plasma or buffer to remove unincorporated oligomer. The washed cells are then infused back into the patient. Other methods for bone marrow purging utilizing antisense oligonucleotide are disclosed in U.S. Pat. No. 5,087,617.

According to a preferred treatment regimen for bone marrow purging, the aspirated bone marrow is contacted daily or twice daily for approximately one to four days with an amount of antisense oligonucleotide effective to overcome the malignant phenotype.

For in vivo administration, the amount of antisense oligonucleotide may vary depending on the nature and extent of the neoplasm, the particular oligonucleotide utilized, and other factors. The actual dosage administered may take into account the size and weight of the patient, whether the nature of the treatment is prophylactic or therapeutic in nature, the age, health and sex of the patient, the route of administration, whether the treatment is regional or systemic, and other factors. Intercellular concentrations of from about 1 to about 200 µg/ml may be employed, preferably from about 10 µg/ml to about 100 µg/ml. The patient should receive a sufficient daily dosage of antisense oligonucleotide to achieve these intercellular concentrations of drug. An effective human intravenous dosage, based upon animal studies employing antisense oligonucleotides targeting other proto-oncogenes in antileukemic therapy, is about 0.4 mg/kg/day. Greater or lesser amounts of oligonucleotide may be administered, as required. Those skilled in the art should be readily able to derive appropriate dosages and schedules of administration to suit the specific circumstance and needs of the patient. It is believed that a course of treatment may advantageously comprise infusion of the recommended daily dose as a continuous intravenous infusion over 7 days. The oligonucleotide may be given for a period of from about 3 to about 28 days, more preferably from about 7 to about 10 days. Those skilled in the art should readily be able to determine the optimal dosage in each case. For modified oligonucleotides, such as phosphorothioate oligonucleotides, which have a half life of from 24 to 48 hours, the treatment regimen may comprise dosing on alternate days. For ex vivo antineoplastic application, such as, for example, in bone marrow purging, the STK-1 antisense oligonucleotides may be administered in amounts effective to kill neoplastic cells. Such amounts may vary depending on the extent to which malignant cells may have arisen or metastasized to the bone marrow, the particular oligonucleotide utilized, the relative sensitivity of the neoplastic cells to the oligonucleotide, and other factors. Concentrations from about 10 to 200 µg/ml per $10_5$ cells may be employed, preferably from about 40 to 150 µg/ml per $10^5$ cells. Supplemental dosing of the same or lesser amounts of oligonucleotide are advantageous to optimize the treatment. Thus, for purging bone marrow containing $2 \times 10^7$ cell per ml of marrow volume, dosages of from about 2 to 40 mg antisense per ml of marrow may be effectively utilized, preferably from about 8 to 24 mg/ml. Greater or lesser amounts of oligonucleotide may be employed.

The effectiveness of the treatment may be assessed by routine methods which are used for determining whether or not remission has occurred. Such methods generally depend upon some combination of morphological, cytochemical, cytogenetic, immunologic and molecular analyses. In addition, remission can be assessed genetically by probing the level of expression of the STK-1 oncogene. The reverse transcriptase polymerase chain reaction methodology can be used to detect even very low numbers of mRNA transcript.

Typically, therapeutic success is assessed by the decrease in the extent of the primary and any metastatic diseases lesions. For solid tumors, decreasing tumor size is the primary indicia of successful treatment. Neighboring tissues may be biopsied to determine the extent to which metastasis has occurred. Tissue biopsy methods are known to those skilled in the art. For non-solid tumors, i.e. the leukemias, treatment is monitored primarily by histological examination of the bone marrow for surviving leukemic cells. However, a significant number of leukemic cells may still exist when marrow examination provides normal results. For this reason, more recent methods for detecting leukemic cells have focused on detecting the presence of the gene for the relevant oncogene, or its corresponding mRNA, in cells of the bone marrow as a more sensitive test. See for example the following U.S. Pat. Nos.: 4,681,840, 4,857,466 and 4,874,853. The presence of even a few copies of the target oncogene can be effectively detected by amplification using reverse transcriptase polymerase chain reaction technology. For a detailed discussion of such methods, see for example, *Cancer: Principles & Practice of Oncology*, edited by V. T. DeVita, S. Hellman and S.A. Rosenberg, J.B. Lippincott Company, Philadelphia, PA (3rd ed., 1989). Methods for diagnosing and monitoring the progress of neoplastic disorders vary depending upon the nature of the particular disease.

An antileukemic treatment plan is proposed as follows. STK-1 phosphorothioate antisense oligonucleotide (24-mer) is administered as a 24-hour continuous intravenous infusion over 7 days. The oligonucleotide is placed in 5% dextrose water and given at a daily dose ranging from about 0.30 to about 2.0 mg/kg/day. Bone marrow aspiration/biopsy is conducted 7, 14 and 21 days after the first cycle of therapy. The patient is evaluated for response on day 21. Additional cycles of therapy may be performed. For such additional cycles of therapy, a bone marrow biopsy will be performed 21 days after the initiation of therapy. Complete remission is determined by the presence of all of the following for a period of at least 4 weeks: (1) a white count below 10,000/$mm^3$ with granulocyte >1000/mm; (2) a platelet count of $\geq 100,000/mm^3$; (3) absence of leukemic blasts from the peripheral blood; (4) a cellularity of bone marrow biopsy of $\geq 20\%$, with maturation of all cell lines; (5) $\geq 5\%$ blasts in the bone marrow; (6) the absence of detectable Auer rods; (7) the absence of organomegaly; (8) the absence of extramedullary leukemia, such as central nervous system or soft tissue involvement.

The practice of the invention is illustrated by the following non-limiting examples.

EXAMPLE 1

Effect of STK-1 Antisense Oligonucleotide Exposure on Normal and Malignant Hematopoietic Progenitor Cell Growth.

A. Inhibition of STK-1 Function with Antisense Oligonucleotides in Normal Hematopoietic Cells.

The cell proliferation stimulating function of STK-1 in normal hematopoietic cells was disrupted with STK-1 antisense oligonucleotides (ODN). Inhibitory effects on the proliferation of cells of varying maturation levels and committed blood cell lineages were assayed. The effect of STK-1 antisense oligonucleotide on hematopoietic progenitor cell colony formation and cellular development was systematically investigated by assessing growth after oligomer exposure. Inhibiting effects on colony-forming unit-erythroid (CFU-E), burstforming unit-erythroid (BFU-E), colony-forming unit-granulocyte/macrophage (CFU-GM), and colony-forming unit-megakaryocyte (CFU-MEG) formation were assayed.

Cells: Human bone marrow cells (BMC) or peripheral blood cells (PB) were obtained from normal healthy, or acute or chronic myelogenous leukemia (AML, CML), volunteers by Ficoll-Hypaque density gradient centrifugation, and were partially enriched for hematopoietic progenitors by positively selecting $CD34^+$cells with immunomagnetic beads (Dynal A.S., Oslo, Norway). The $CD34^+$cells were suspended in supplemented alpha medium and incubated with mouse anti-HPCA-I antibody in 1:20 dilution, 45 minutes, at 4° C. with gentle inverting of tubes. Cells were washed three times in supplemented alpha medium, and then incubated with beads coated with the Fc fragment of goat anti-mouse $IgG_1$ (75 µl of immunobeads/$10^7$ $CD34^+$MNC). After 45 minutes of incubation (4° C.), cells adherent to the beads were positively selected using a magnetic particle concentrator as directed by the manufacturer.

Oligodeoxynucleotides: Unmodified, 18-nucleotide oligodeoxynucleotides were synthesized as previously reported (Gewirtz et al., *Science* 242, 1303–1306 (1988)). In brief, oligomers were synthesized on an Applied Biosystems 380B DNA synthesizer by means of a βcyanoethyl phosphoramidite chemistry. Antisense oligonucleotides were targeted to different regions of STK-1 mRNA sequence:

(i) SEQ ID NO:3, an antisense ("AS") oligonucleotide targeting nucleotides 1 to 18 of SEQ ID NO:1 5' non-coding region upstream ("US") of the coding region;

(ii) SEQ ID NO:4, an antisense oligonucleotide targeting nucleotides 58–75, corresponding to codons 1–6 of the coding region i.e. translation initiation site ("TS");

(iii) SEQ ID NO:5, an antisense oligonucleotide targeting nucleotides 121 to 138, a site about 60 nucleotides downstream ("DS") of the translation initiation site;

(iv) SEQ ID NO:6, the sense ("S") oligonucleotide corresponding to the target SEQ ID NO:3;

(v) SEQ ID NO:7, the "S" oligonucleotide corresponding to the target SEQ ID NO:4;

(vi) SEQ ID NO:8, the "S" oligonucleotide corresponding to the target SEQ ID NO:5;

(vii) SEQ ID NO:9, a scrambled sense "SCR" oligonucleotide corresponding to SEQ ID NO:3;

(viii) SEQ ID NO:10, a "SCR" oligonucleotide corresponding to SEQ ID NO:4; and (ix) SEQ ID NO:11, a "SCR" oligonucleotide corresponding to SEQ ID NO:5.

The scrambled sense sequence consisted of an oligonucleotide with a nucleotide content identical to the corresponding antisense sequence but with the bases in a random order. Oligomers were purified by ethanol precipitation and multiple washes in 70% ethanol. They were then lyophilized to dryness and redissolved in culture medium prior to use at a concentration of 1 µg/µl (170 µM).

Oligomer Treatment of Cells: Cells were exposed to oligomers as previously described (Gewirtz et al., Science 242, 1303–1306 (1988)). About $2 \times 10^4$ CD34$^+$cells were incubated in 5 ml polypropylene tubes (Fisher Scientific, Pittsburgh, Pa.) in a total volume of 0.4 ml of Iscove's modified Dulbecco's medium (IMDM) containing 2% bovine calf serum and 10 mM Hepes buffer. Oligomers having sequences according to SEQ ID NOS:3–11 were each added to separate tubes of cells at time zero (20–100 µg/ml ), and 50% of the initial dose was added again 18 hours later (final total concentration ~5–26 µM). Thirty-six hours after the first addition of oligomers, the cells were prepared for plating and culturing directly in colony forming assays (plasma clot or methylcellulose cultures) or on bone marrow stromal cell feeder layers (LTBMC). Cells ($1 \times 10^4$ CD34$^+$MNC per dish) were not washed before plating. Control cultures were manipulated in an identical manner but were not treated with oligomers. CD34$^+$cells were exposed to increasing doses of AS oligonucleotides (SEQ ID NOS:3–5). As a control, CD34$^+$cells were exposed to S oligonucleotides (SEQ ID NOS:6–8), and Scr oligonucleotides (SEQ ID NOS:9–11) equivalent to the highest AS dose employed.

Colony Assays: Assays for hematopoietic progenitor cells of varying lineages were carried out essentially as reported (above). In brief, cells ($2 \times 10^4$ CD34$^+$) were re-suspended in IMDM supplemented with 30% bovine calf serum, 1% BSA, $10^{-4}$ M mercaptoethanol, and 10% citrated bovine plasma (Hyclone Laboratories, Denver, Colo.). Addition of the appropriate recombinant human growth factors allowed for stimulation of the following cell types:

CFU-E:5 U/ml EPO;

BFU-E:20 U/ml IL-3 and 5 U/ml EPO, or 100 ng/ml SCF and 5 U/ml EPO;

CFU-GM:20 U/ml IL-3 and 5 ng/ml granulocytemacrophage colony stimulating factor;

CFU-MEG:20 U/ml IL-3 and 100 ng/ml IL-6.

One ml volumes were cultured in 35 mm petri dishes at 37° C., 5% CO$_2$, and 95% humidity. CFU-E colonies were scored at day 7, BFU-E colonies at day 14, CFU-MEG at day 12, and CFU-GM at day 11 of incubation. Colony identification was carried out as previously described (above).

Statistics: Statistical significance of differences between means of test groups was assessed by Mann-Whitney non-parametric analysis using a statistical software package (Instat, Graph Pad Software, Inc., San Diego, Calif.; StatView 4.0 Abacus Concepts, Berkley, Calif.).

Figure 4A:
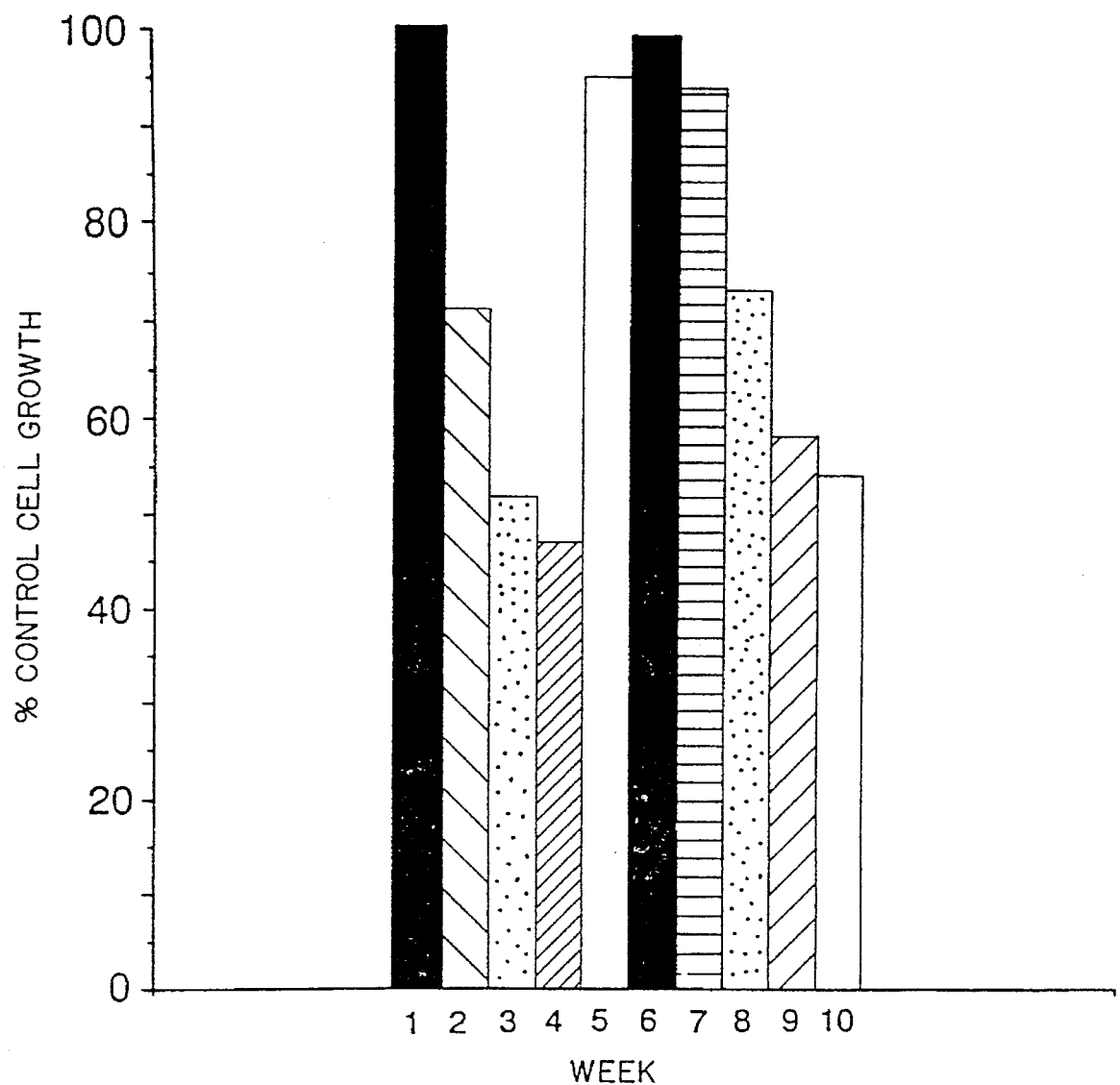
FIG. 4A is a histogram of the effect of STK-1 antisense oligomers on normal hematopoietic cell colony growth. CD34+ cells were exposed to STK-1 oligomers at the indicated concentrations (e.g. "U.S. AS 20-10" means upstream antisense oligomers at 10 82 g/ml for 18 hours and then 20 μg/ml for an additional 18 hours). After exposure to the antisense oligomers for 36 hours the CD34+ cells were assayed for colony-forming unit-granulocyte-megakaryocyte (CFU-GM) colonies.

Results: Neither S nor Scr oligodeoxynucleotides (ODNs) inhibited colony formation. In contrast, dose dependent inhibition was noted with AS ODNs. At the highest dosed employed, CFU-GM colony formation was inhibited 53% (p<0.001), and 46% (p=0.003) respectively, when sites upstream and downstream of the translation initiation site were targeted (FIG. 4A). In Figure 4A "US AS 20–10"means upstream antisense oligomer at 20 µg/ml for 18 hours and then 10 µg/ml for an additional 18 hours. The AS ODN targeting the translation initiation ("TS") site (SEQ ID NO:4) gave no significant inhibition. When treated in an identical manner, STK-1 US inhibited BFU-E 57% (p<0.001), while the STK-1 AS ODN targeting the downstream ("DS") target (SEQ ID NO:5) inhibited 40% (p=0.002) (data not shown). Again, targeting the translation initiation site was without effect. Similar inhibition was also seen when the experiments were carried out on adherent- and T-lymphocytedepleted MNC (A-T-MNC).

The inhibitory effects of STK-1 antisense oligonucleotides on STK-1 in a less mature hematopoietic cell population, CFU-GEMM, was also analyzed (FIG. 4B). Colony formation by this progenitor was decreased by ~80% (p=0.001) targeting the upstream sequence and, 62% (p=0.07) targeting the downstream sequence. Immature progenitor cells cultured in the presence of STK-1 TS antisense oligonucleotide were not inhibited in a statistically significant manner (p=0.18). Neither S nor Scr sequences inhibited CFU-GEMM colony formation by the primitive hematopoietic cells. See FIG. 4B for results.

These results demonstrate that STK-1 function was necessary for growth of myeloid and erythroid progenitor cells. Also, early progenitor cells (CFU-GEMM) are more dependent on the putative signalling function of the STK-1 protein than later progenitor cells (CFU-GM and BFU-E). The results also suggest that the upstream sequence of the message, that is, the 5' non-coding region, is likely the best region for selecting region targets for antisense mediated disruption of STK-1 function.

B. Inhibition of Colony Formation in Long Term Bone Marrow Cultures by STK-1 Antisense Oligonucleotides.

Figure 4C:
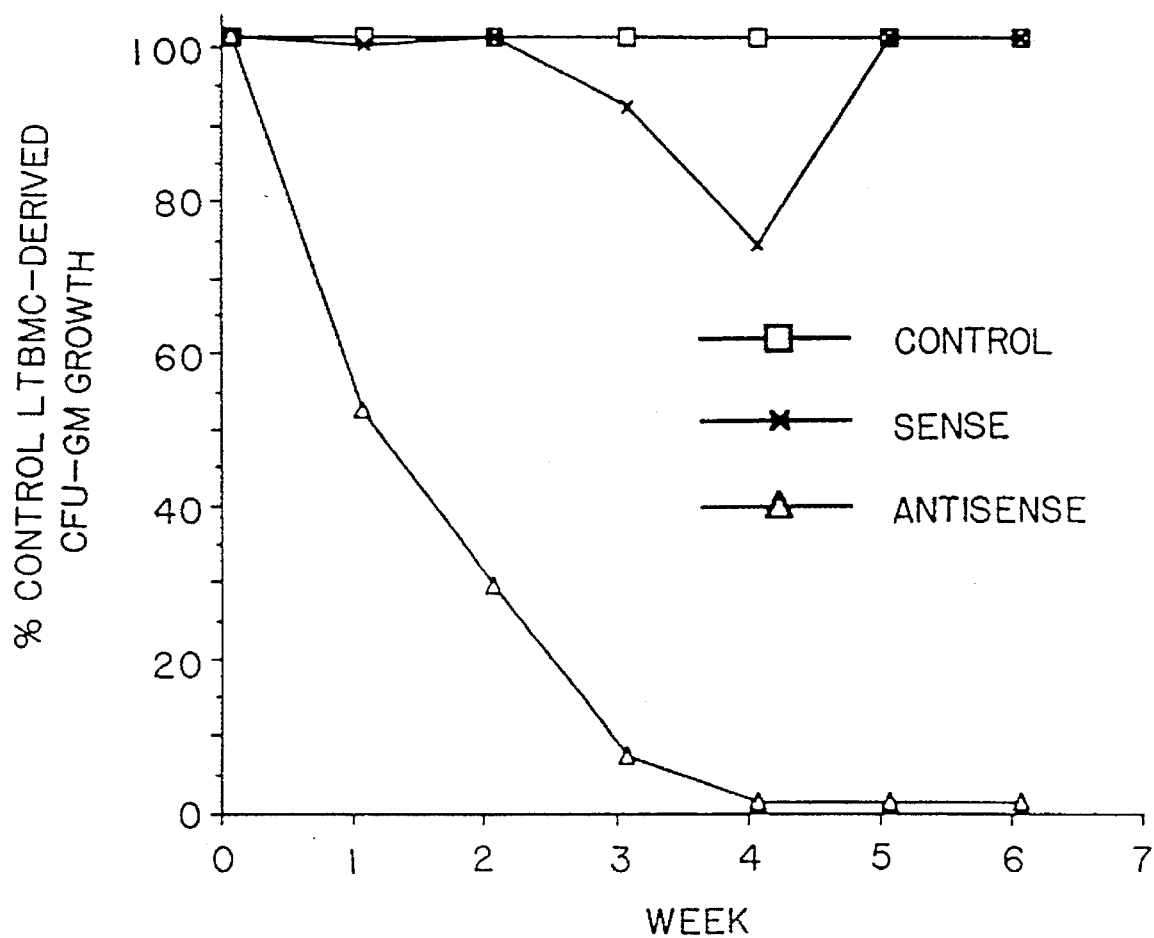
FIG. 4C is a plot of the long term inhibitory effects of STK-1 antisense oligonucleotides on the formation of CFU-GM colonies in a long-term bone marrow culture (LTBMC). The CD34+ cells were exposed to the upstream antisense, sense, and control (scrambled) oligomers at 100 μg/ml for 18 hours and then 50 μg/ml for an additional 18 hours. They were then plated on irradiated bone marrow stromal cell feeder layers and assayed for CFU-GM colonies at weekly intervals. The graph shows that the ability of a LTBMC to form CFU-GM colonies was rapidly inhibited by exposure to STK-1 antisense oligonucleotides. CFU-GM colony formation was decreased by 95% in 3 weeks and completely inhibited in about 4 weeks.

STK-1 function is most susceptible to anti-sense inhibition in early progenitor cells. Long term bone marrow cultures (LTBMC) were established and the ability of stem-cell-like progenitors in such cultures to give rise to CFU-GM after exposure to STK-1 US ODN was assayed. For the LTBMC assay, the cultures were plated on a bone marrow cell feeder layer. The cultures were agitated at weekly intervals and one-half of each culture was removed and assayed for CFU-GM colony formation. As shown in FIG. 4C, the ability of LTBMC to give rise to CFU-GM was inhibited almost immediately. Colony formation decreased by ~95% by week 3 and was essentially absent by week 4. Thus, STK-1 antisense inhibition is highly effective in very early hematopoietic cells close to, or at the level of, the hematopoietic stem cell.

C. STK-1 Antisense Oligonucleotide Inhibition of ML-1 Leukemia Cell Proliferation.

Exposure of the ML-1 (AML) cell line to STK-1 antisense oligonucleotides under the conditions set forth in Example 1(A) and (B), above resulted in the absence of the STK-1 message. The STK-1 message was assayed for by RT-PCR (data not shown). By contrast, control ML-1 leukemia cells not exposed to AS oligonucleotides expressed STK-1. Further, the growth of the ML-1 leukemia cells exposed the AS oligo-nucleotides was inhibited. This indicated that the growth of ML-1 leukemia cells is inhibited by inhibiting the STK-1 message with the STK-1 antisense oligonucleotides.

EXAMPLE 2

STK-1 Antisense Oligonucleotide Inhibition of STK-1 Expression by Neoplastic Cells.

A. STK-1 Expression by Neoplastic Cells.

The following human tumor cell lines were screened for STK-1 expression: HS-4019 (melanoma), HTB19 (breast), CRL-1435 (prostate), A-549 (mesothelioma), and NB-69 (neuroblastoma). These lines were chosen because in the aggregate they represent tissues of endo-, ecto-, and mesodermal origin, respectively.

Total cellular RNA was extracted from $1\times10^6$ cells of each using RNAzol and chloroform (1:10). The RNA pellet obtained after overnight precipitation at $-20°$ C. was washed three times in ethanol and then reverse transcribed with random hexamers. The resulting cDNA was PCR amplified with STK-1 specific 5' and 3' primers corresponding to nucleotides 97–128 and 304–325 respectively. PCR reactions were run for 40 cycles after which the products were transferred to nylon filters for probing with a $^{32}$P end-labeled 24 mer oligonucleotide corresponding to STK-1 mRNA nucleotides 181–205. RNA from the human leukemia cell line ML-1 was employed as a positive control. A negative control for the detection of contaminated reactions was also run simultaneously.

All neoplastic cell lines examined were found to express STK-1 as evidenced by detection of the predicted 228 nucleotide PCR product. Accordingly, STK-1 expression is present in tumor cell lines as well as in normal immature cells of hematopoietic lineage.

B. STK-1 Antisense Inhibition of Melanoma Cell Growth

Exposure of the neoplastic cell lines described in Example 2(A) to STK-1 antisense oligonucleotides lead to inhibition of cell growth and cell death, as described in the following experiment.

Figure 5:
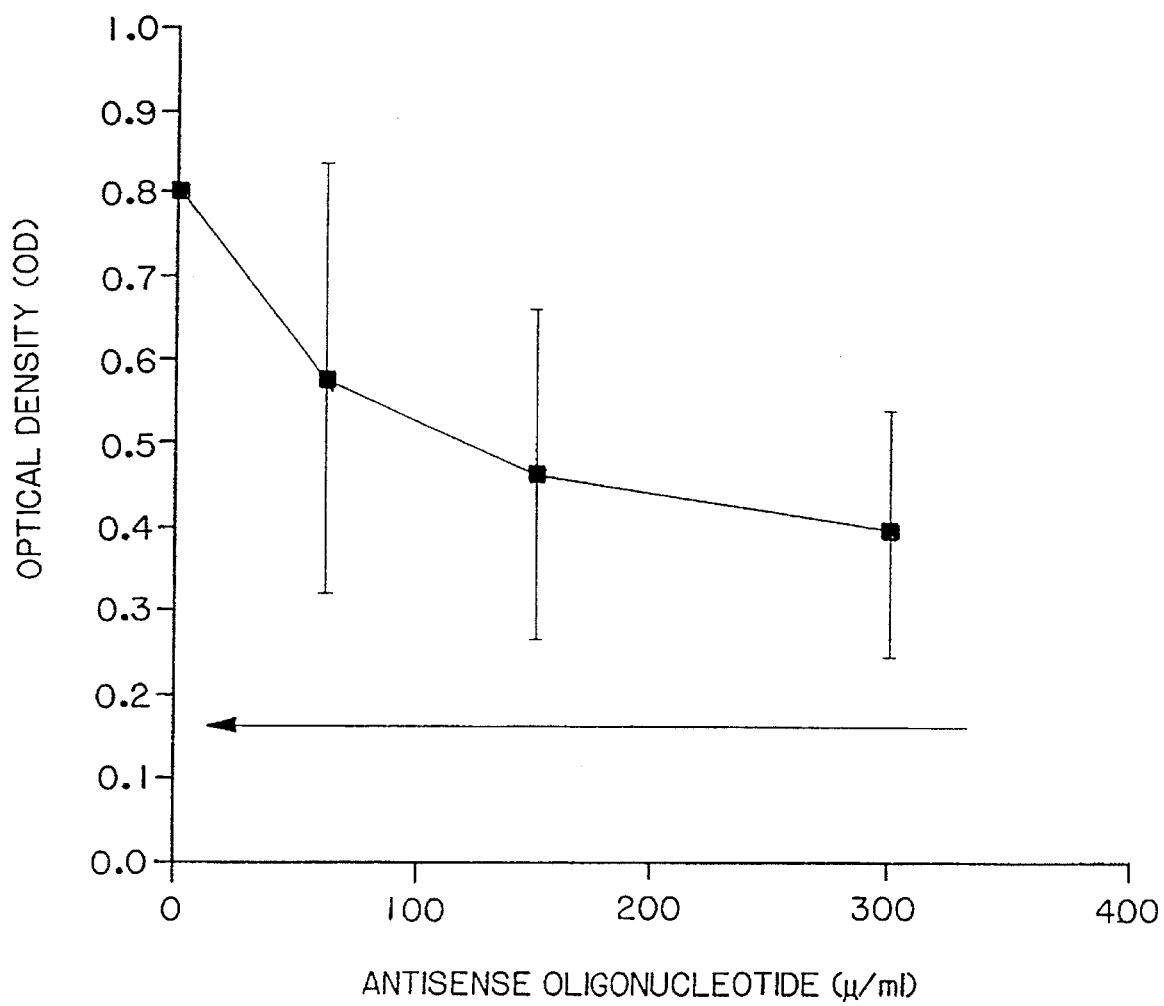
FIG. 5 is a graph showing the ability of STK-1 antisense oligonucleotides to inhibit cell growth and cause cellular death of HS-294 T-melanoma cells. The x-axis indicates the concentration of the antisense oligonucleotide, and the y-axis indicates the optical density (OD) of the cell culture. The arrow indicates the baseline optical density of the media.

The effect of STK-1 antisense oligonucleotides on the growth of HS-294 T melanoma cells was determined by MTT as follows. Cells were seeded into microliter dishes (500 cells per well), allowed to adhere for 24 hours, and then treated with oligonucleotides at a final concentration as indicated on the x-axis in FIG. 5. The effect on growth is measured as a function of optical density (OD) on the eighth day of culturing. The OD is indicated on the y-axis in FIG. 5. The effect of sense and scrambled (SCR) was also measured. The baseline OD reading (indicated by an arrow in FIG. 5) is of the well containing only tissue culture medium. The greater the OD reading above the baseline, the greater is the cellular concentration in the culture. The results presented are mean optical density readings averaged from four separate experiments, each carried out in triplicate. The graph in FIG. 5 demonstrates the inhibitory effect of STK-1 antisense oligonucleotides on the eighth day of culture. The effect of sense and scrambled sense oligonucleotides was also measured as controls. The OD of the sense oligonucleotide control cell culture was 0.88 on day eight. The OD of the scrambled oligonucleo-tide control cell culture was 0.72 on day eight.

C. STK-1 Antisense Inhibition of Prostate Cancer Cell Growth

Figure 6:
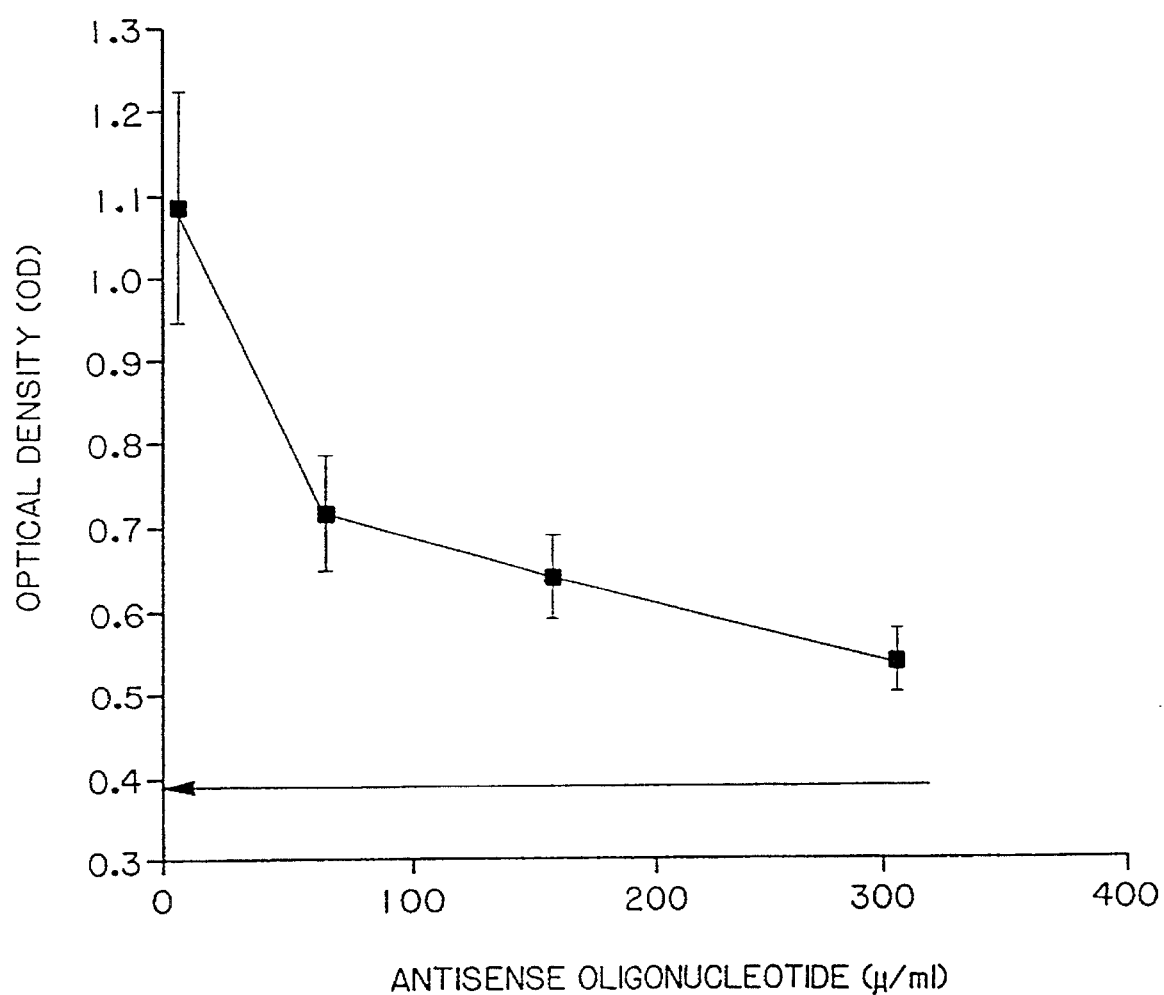
FIG. 6 shows the ability of STK-1 antisense oligonucleotides to inhibit cell growth and cause cellular death of CRL-1435 prostate cancer cells. The x-axis indicates the concentration of the antisense oligonucleotide, and the y-axis indicates the optical density (OD) of the cell culture. The arrow indicates the baseline optical density of the media.

The effect of STK-1 antisense oligonucleotides on the growth of CRL 1435 prostate cancer cells was assayed as follows. Cells were seeded into microliter dishes (500 cells per well) allowed to adhere for 24 hours and then treated with oligomers at a final concentration as indicated on the x-axis in FIG. 6. The effect on growth is measured as in Example 1B, above. The results presented in FIG. 6 are the mean optical density readings on the eighth day of culturing from three separate experiments, each carried out in triplicate. The effect of sense and scrambled (SCR) was also measured as controls. The OD of the sense oligonucleotide control cell culture was 1.03 on day eight. The OD of the scrambled oligonucleotide control cell culture was 1.16 on day eight.

EXAMPLE 3

Western Blot Analysis of Proteins from Cell Lines Which Express STK-1.

Western blots of protein from the 3T3 cell line were used as positive and negative controls in assays for cell lines which express STK-1. Transfected 3T3 cells, which provide protein for a negative control Western blot in the STK-1 protein assay, were obtained as follows. The 3T3 cells were transfected with a vector as described in FIG. 2, but absent the STK-1 construct. The transfected 3T3 cells which express STK1 were obtained by transfecting 3T3 cells with the same vector line, but with the vector including the STK-1 construct. The 3T3 cells with the STK-1 construct express the STK-1 protein and serve as a positive control in the Western blot assay for the STK-1 protein.

Proteins from the two types of transfected 3T3 cells were processed and Western blots prepared as follows. Approximately equal amounts of protein were extracted from positive and negative control 3T3 cells and electrophoresed through 4–12% polyacrylamide gels. After electrophoresis, the proteins were transferred to nitrocellulose by blotting. The blots were then incubated with 5µg/ml of affinity purified rabbit polyclonal antibody raised against a peptide from the kinase insert region of STK-1. After washing, the incubated filters were exposed to anti-rabbit IG conjugated to peroxidase and developed as per the manufacturer's protocol (ECL, Amersham).

Figure 3A:
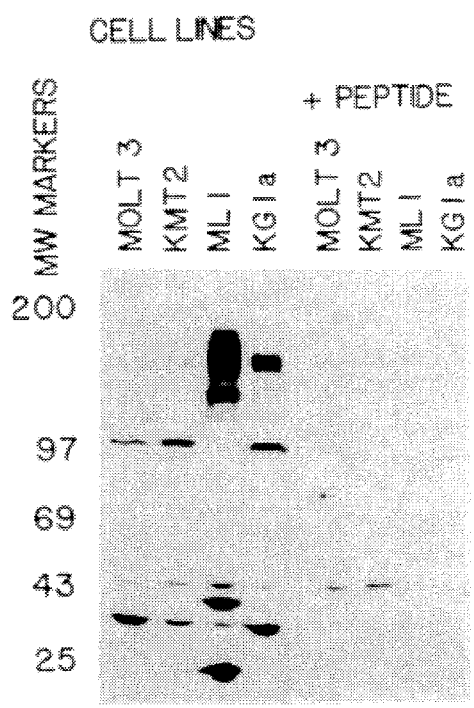
FIG. 3A is a Western blot of proteins from cell lines which express STK-1 and from cell lines which do not express STK-1. Approximately equal amounts of protein were extracted from the indicated cell lines and electrophoresed through 4–12% polyacrylamide gels. After electrophoresis, the proteins were transferred to nitrocellulose by blotting. The blots were then incubated with 5 μg/ml of affinity purified rabbit polyclonal antibody raised against a peptide from the kinase insert region. The lanes marked with "+ peptide" indicate that the peptide used to generate antibody was added to the antibody at 20 μg/ml prior to incubating the antibody with nitrocellulose filter. The "+ peptide" lanes were otherwise treated in an identical manner to the lanes on the left. After washing, the incubated filters were exposed to anti-rabbit IG conjugated to peroxidase and developed as per the manufacturer's protocol (ECL, Amersham).
Figure 3B:
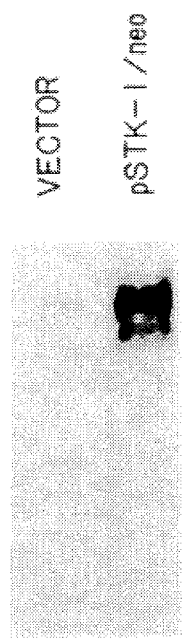
FIG. 3B is a Western blot of the protein from the 3T3 cell line. Lane 1 is a blot of the protein from 3T3 cells transfected with a vector as described for FIG. 2, above, but absent the STK-1 construct. Lane 2 is a blot of protein from 3T3 cells transfected with the same vector line, but including the STK-1 construct, which expresses STK-1. Proteins from the transfected 3T3 cells were processed and Western blots prepared in the same manner as described for proteins in FIG. 3A, above.

Lane 1 of FIG. 3B is a Western blot of the protein from the 3T3 cells which were transfected with the empty vector. Lane 2 of FIG. 3B is a blot of the protein from 3T3 cells which were transfected with the vector including the STK-1 construct. Lane 1 illustrates a negative control Western blot of cells which do not express STK-1. Lane 2 illustrates a positive control Western blot of cells which express the STK-1 protein.

The protein from cell lines suspected of expressing STK-1 was extracted and assayed for STK-1 expression by the Western blots assay described above. Approximately equal amounts of protein from the cell lines indicated in FIG. 3A were extracted and Western blots obtained. The protein from the 3T3 positive and negative control cells were used as positive and negative controls in the assay.

The results for the assayed cells are shown in FIG. 3A. The lanes marked with "+ peptide" indicate that the peptide used to generate antibody was added to the antibody at 20µg/ml prior to incubating the antibody with nitrocellulose filter. The "+ peptide" lanes were otherwise treated in an identical manner to the lanes on the left. The positive and negative control Western blots of positive and negative control 3T3 cells were substantially as illustrated in FIG. 3B (results not shown).

EXAMPLE 4

Bone Marrow Purging with STK-1 Antisense Oligonucleotide

Bone marrow is harvested from the iliac bones of a donor under general anesthesia in an operating room using standard techniques. Multiple aspirations are taken into heparinized syringes. Sufficient marrow is withdrawn so that the marrow recipient will be able to receive about $4 \times 10^8$ to about $8 \times 10^8$ processed marrow cells per kg of body weight. Thus, about 750 to 1000 ml of marrow is withdrawn. The aspirated marrow is transferred immediately into a transport medium (TC-199, Gibco, Grand Island, New York) containing 10,000 units of preservative-free heparin per 100 ml of medium. The aspirated marrow is filtered through three progressively finer meshes until a single cell suspension results, i.e., a suspension devoid of cellular aggregates, debris and bone particles. The filtered marrow is then processed further into an automated cell separator (e.g., Cobe 2991 Cell Processor) which prepares a "buffy coat" product, (i.e., leukocytes devoid of red cells and platelets). The buffy coat preparation is then placed in a transfer pack for further processing and storage. It may be stored until purging in liquid nitrogen using standard procedures. Alternatively, purging can be carried out immediately, then the purged marrow may be stored frozen in liquid nitrogen until it is ready for transplantation.

The purging procedure may be carried out as follows. Cells in the buffy coat preparation are adjusted to a cell concentration of about $2 \times 10^7$/ml in TC-199 containing about 20% autologous plasma. STK-1 antisense oligodeoxynucleotide, for example, in a concentration of about 8 mg/ml, is added to the transfer packs containing the cell suspension. Recombinant human hematopoietic growth factors, e.g., rH IL-3 or rH GMCSF, may be added to the suspension to stimulate growth of hematopoietic neoplasms and thereby increase their sensitivity STK-1 antisense oligonucleotide toxicity. The transfer packs are then placed in a 37° C. water bath and incubated for 18–24 hours with gentle shaking. The cells may then either be frozen in liquid nitrogen or washed once at 4° C. in TC-199 containing about 20% autologous plasma to remove unincorporated oligomer. Washed cells are then infused into the recipient. Care must be taken to work under sterile conditions wherever possible and to maintain scrupulous aseptic techniques at all times.

The present invention may be embodied in other specific forms without departing from the spirit or essential attributes thereof and, accordingly, reference should be made to the appended claims, rather than to the foregoing specification, as indicating the scope of the invention.

All references cited herein with respect to synthetic, reparative and analytical procedures are incorporated herein by reference.

We claim:

1. An oligonucleotide having the nucleotide sequence SEQ ID NO:3 or SEQ ID NO:5.

2. An oligonucleotide according to claim 1 wherein the oligonucleotide is an alkylphosphonate oligonucleotide or phosphorothioate oligonucleotide.

3. An oligonucleotide according to claim 1 wherein the oligonucleotide is an oligodeoxynucleotide.

4. An artificially-constructed gene comprising a transcriptional promotor segment and a segment containing a STK-1 DNA in inverted orientation such that transcription of said artificially-constructed gene produces RNA having the nucleotide sequence SEQ ID NO:3 or SEQ ID NO:5.

5. A gene according to claim 4 wherein the promotor segment comprises SV40 promotor.

6. A method for inhibiting the proliferation of malignant cells in vitro, which express STK-1, comprising introducing into such cells an artificially-constructed gene according to claim 3.

7. A method according to claim 6 wherein the artificially-constructed gene is introduced into said cells by transfection, by a transducing viral vector or by microinjection.

8. A method of inhibiting the proliferation of cells in vitro comprising contacting said cells with a proliferation inhibiting amount of an oligonucleotide according to claim 1.

9. A method according to claim 8 wherein the cells are malignant cells.

10. A method according to claim 8 wherein the cells are hematopoietic cells.

11. A method according to claim 10 wherein the cells are malignant cells.

12. A method according to claim 8 wherein the oligonucleotide has the nucleotide sequence SEQ ID NO:3.

13. A method according to claim 8 wherein the oligonucleotide has the nucleotide sequence SEQ ID NO:5.

14. A method of inhibiting in vitro the growth of neoplastic cells in bone marrow comprising contacting bone marrow cells with a neoplastic cell growth-inhibiting amount of an oligonucleotide according to claim 1.

15. A method according to claim 14 wherein the neoplastic cells comprise leukemic cells.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 3476 nucleotides
        ( B ) TYPE: nucleic acid
        ( C ) STRANDEDNESS: single stranded
        ( D ) TOPOLOGY: linear ( x i ) SEQUENCE DESCRIPTION: SEQ ID NO:1:

```
CGAGGCGGCA  TCCGAGGGCT  GGGCCGGCGC  CCTGGGGGAC  CCCGGGCTCC   50
GGAGGCCATG  CCGGCGTTGG  CGCGCGACGC  GGGCACCGTG  CCGCTGCTCG  100
TTGTTTTTTC  TGCAATGATA  TTTGGGACTA  TTACAAATCA  AGATCTGCCT  150
GTGATCAAGT  GTGTTTAAT   CAATCATAAG  AACAATGATT  CATCAGTGGG  200
GAAGTCATCA  TCATATCCCA  TGGTATCAGA  ATCCCCGGAA  GACCTCGGGT  250
GTGCGTTGAG  ACCCCAGAGC  TCAGGGACAG  TGTACGAAGC  TGCCGCTGTG  300
GAAGTGGATG  TATCTGCTTC  CATCACACTG  CAAGTGCTGG  TCGATGCCCC  350
AGGGAACATT  TCCTGTCTCT  GGGTCTTTAA  GCACAGCTCC  CTGAATTGCC  400
AGCCACATTT  TGATTTACAA  AACAGAGGAG  TTGTTTCCAT  GGTCATTTTG  450
AAAATGACAG  AAACCCAAGC  TGGAGAATAC  CTACTTTTTA  TTCAGAGTGA  500
AGCTACCAAT  TACACAATAT  TGTTTACAGT  GAGTATAAGA  AATACCCTGC  550
TTTACACATT  AAGAAGACCT  TACTTTAGAA  AAATGGAAAA  CCAGGACGCC  600
CTGGTCTGCA  TATCTGAGAG  CGTTCCAGAG  CCGATCGTGG  AATGGGTGCT  650
TTGCGATTCA  CAGGGGAAA   GCTGTAAAGA  AGAAAGTCCA  GCTGTTGTTA  700
AAAAGGAGGA  AAAAGTGCTT  CATGAATTAT  TTGGGACGGA  CATAAGGTGC  750
TGTGCCAGAA  ATGAACTGGG  CAGGGAATGC  ACCAGGCTGT  TCACAATAGA  800
```

-continued

```
TCTAAATCAA ACTCCTCAGA CCACATTGCC ACAATTATTT CTTAAAGTAG    850
GGGAACCCTT ATGGATAAGG TGCAAAGCTG TTCATGTGAA CCATGGATTC    900
GGGCTCACCT GGGAATTAGA AAACAAAGCA CTCGAGGAGG GCAACTACTT    950
TGAGATGAGT ACCTATTCAA CAAACAGAAC TATGATACGG ATTCTGTTTG   1000
CTTTTGTATC ATCAGTGGCA AGAAACGACA CCGGATACTA CACTTGTTCC   1050
TCTTCAAAGC ATCCCAGTCA ATCAGCTTTG GTTACCATCG TAGAAAGGG    1100
ATTTATAAAT GCTACCAATT CAAGTGAAGA TTATGAAATT GACCAATATG   1150
AAGAGTTTTG TTTTTCTGTC AGGTTTAAAG CCTACCCACA AATCAGATGT   1200
ACGTGGACCT TCTCTCGAAA ATCATTTCCT TGTGAGCAAA AGGGTCTTGA   1250
TAACGGATAC AGCATATCCA AGTTTTGCAA TCATAAGCAC CAGCCAGGAG   1300
AATATATATT CCATGCAGAA AATGATGATG CCCAATTTAC CAAAATGTTC   1350
ACGCTGAATA TAAGAAGGAA ACCTCAAGTG CTCGCAGAAG CATCGGCAAG   1400
TCAGGCGTCC TGTTTCTCGG ATGGATACCC ATTACCATCT TGGACCTGGA   1450
AGAAGTGTTC AGACAAGTCT CCCAACTGCA CAGAAGAGAT CACAGAAGGA   1500
GTCTGGAATA GAAAGGCTAA CAGAAAAGTG TTTGGACAGT GGGTGTCGAG   1550
CAGTACTCTA AACATGAGTG AAGCCATAAA AGGGTTCCTG GTCAAGTGCT   1600
GTGCATACAA TTCCCTTGGC ACATCTTGTG AGACGATCCT TTTAAACTCT   1650
CCAGGCCCCT TCCCTTTCAT CCAAGACAAC ATCTCATTCT ATGCAACAAT   1700
TGGTGTTTGT CTCCTCTTCA TTGTCGTTTT AACCCTGCTA ATTTGTCACA   1750
AGTACAAAAA GCAATTTAGG TATGAAAGCC AGCTACAGAT GGTACAGGTG   1800
ACCGGCTCCT CAGATAATGA GTACTTCTAC GTTGATTTCA GAGAATATGA   1850
ATATGATCTC AAATGGGAGT TTCCAAGAGA AAATTTAGAG TTTGGGAAGG   1900
TACTAGGATC AGGTGCTTTT GGAAAAGTGA TGAACGCAAC AGCTTATGGA   1950
ATTAGCAAAA CAGGAGTCTC AATCCAGGTT GCCGTCAAAA TGCTGAAAGA   2000
AAAAGCAGAC AGCTCTGAAA GAGAGGCACT CATGTCAGAA CTCAAGATGA   2050
TGACCCAGCT GGGAAGCCAC GAGAATATTG TGAACCTGCT GGGGGCGTGC   2100
ACACTGTCAG GACCAATTTA CTTGATTTTT GAATACTGTT GCTATGGTGA   2150
TCTTCTCAAC TATCTAAGAA GTAAAAGAGA AAAATTTCAC AGGACTTGGA   2200
CAGAGATTTT CAAGGAACAC AATTTCAGTT TTTACCCCAC TTTCCAATCA   2250
CATCCAAATT CCAGCATGCC TGGTTCAAGA GAAGTTCAGA TACACCCGGA   2300
CTCGGATCAA ATCTCAGGGC TTCATGGGAA TTCATTTCAC TCTGAAGATG   2350
AAATTGAATA TGAAAACCAA AAAAGGCTGG AAGAAGAGGA GGACTTGAAT   2400
GTGCTTACAT TTGAAGATCT TCTTTGCTTT GCATATCAAG TTGCCAAAGG   2450
AATGGAATTT CTGGAATTTA AGTCGTGTGT TCACAGAGAC CTGGCCGCCA   2500
GGAACGTGCT TGTCACCCAC GGGAAAGTGG TGAAGATATG TGACTTTGGA   2550
TTGGCTCGAG ATATCATGAG TGATTCCAAC TATGTTGTCA GGGGCAATGC   2600
CCGTCTGCCT GTAAAATGGA TGGCCCCCGA AAGCCTGTTT GAAGGCATCT   2650
ACACCATTAA GAGTGATGTC TGGTCATATG GAATATTACT GTGGGAAATC   2700
TTCTCACTTG GTGTGAATCC TTACCCTGGC ATTCCGGTTG ATGCTAACTT   2750
CTACAAACTG ATTCAAAATG GATTTAAAAT GGATCAGCCA TTTTATGCTA   2800
```

-continued

```
CAGAAGAAAT ATACATTATA ATGCAATCCT GCTGGGCTTT TGACTCAAGG    2850
AAACGGCCAT CCTTCCCTAA TTTGACTTCG TTTTTAGGAT GTCAGCTGGC    2900
AGATGCAGAA GAAGCGATGT ATCAGAATGT GGATGGCCGT GTTTCGGAAT    2950
GTCCTCACAC CTACCAAAAC AGGCGACCTT TCAGCAGAGA GATGGATTTG    3000
GGGCTACTCT CTCCGCAGGC TCAGGTCGAA GATTCGTAGA GGAACAATTT    3050
AGTTTTAAGG ACTTCATCCC TCCACCTATC CCTAACAGGC TGTAGATTAC    3100
CAAAACAAGA TTAATTTCAT CACTAAAAGA AAATCTATTA TCAACTGCTG    3150
CTTCACCAGA CTTTTCTCTA GAAGCCGTCT GCGTTACTC TTGTTTTCAA     3200
AGGGACTTTT GTAAAATCAA ATCATCCTGT CACAAGGCAG GAGGAGCTGA    3250
TAATGAACTT TATTGGAGCA TTGATCTGCA TCCAAGGCCT TCTCAGGCCG    3300
GCTTGAGTGA ATTGTGTACC TGAAGTACAG TATATTCTTG TAAATACATA    3350
AAACAAAAGC ATTTTGCTAA GGAGAAGCTA ATATGATTTT TTAAGTCTAT    3400
GTTTTAAAAT AATATGTAAA TTTTTCAGCT ATTTAGTGAT ATATTTATG     3450
GGTGGGAATA AAATTTCTAC TACAGA                              3476
```

( 2 ) INFORMATION FOR SEQ ID NO:2:

( i ) SEQUENCE CHARACTERISTICS:
        ( A ) LENGTH: 993 amino acids
        ( B ) TYPE: amino acid
        ( D ) TOPOLOGY: linear ( x i ) SEQUENCE DESCRIPTION: SEQ ID NO:2:

```
Met Pro Ala Leu Ala Arg Asp Ala Gly Thr Val Pro Leu Leu Val
                  5                  10                 15

Val Phe Ser Ala Met Ile Phe Gly Thr Ile Thr Asn Gln Asp Leu
                 20                  25                 30

Pro Val Ile Lys Cys Val Leu Ile Asn His Lys Asn Asn Asp Ser
                 35                  40                 45

Ser Val Gly Lys Ser Ser Tyr Pro Met Val Ser Glu Ser Pro
                 50                  55                 60

Glu Asp Leu Gly Cys Ala Leu Arg Pro Gln Ser Ser Gly Thr Val
                 65                  70                 75

Tyr Glu Ala Ala Ala Val Glu Val Asp Val Ser Ala Ser Ile Thr
                 80                  85                 90

Leu Gln Val Leu Val Asp Ala Pro Gly Asn Ile Ser Cys Leu Trp
                 95                 100                105

Val Phe Lys His Ser Ser Leu Asn Cys Gln Pro His Phe Asp Leu
                110                 115                120

Gln Asn Arg Gly Val Val Ser Met Val Ile Leu Lys Met Thr Glu
                125                 130                135

Thr Gln Ala Gly Glu Tyr Leu Leu Phe Ile Gln Ser Glu Ala Thr
                140                 145                150

Asn Tyr Thr Ile Leu Phe Thr Val Ser Ile Arg Asn Thr Leu Leu
                155                 160                165

Tyr Thr Leu Arg Arg Pro Tyr Phe Arg Lys Met Glu Asn Gln Asp
                170                 175                180

Ala Leu Val Cys Ile Ser Glu Ser Val Pro Glu Pro Ile Val Glu
                185                 190                195

Trp Val Leu Cys Asp Ser Gln Gly Glu Ser Cys Lys Glu Glu Ser
                200                 205                210
```

```
Pro  Ala  Val  Val  Lys  Lys  Glu  Glu  Lys  Val  Leu  His  Glu  Leu  Phe
                    215                 220                           225
Gly  Thr  Asp  Ile  Arg  Cys  Cys  Ala  Arg  Asn  Glu  Leu  Gly  Arg  Glu
                    230                 235                           240
Cys  Thr  Arg  Leu  Phe  Thr  Ile  Asp  Leu  Asn  Gln  Thr  Pro  Gln  Thr
                    245                 250                           255
Thr  Leu  Pro  Gln  Leu  Phe  Leu  Lys  Val  Gly  Glu  Pro  Leu  Trp  Ile
                    260                 265                           270
Arg  Cys  Lys  Ala  Val  His  Val  Asn  His  Gly  Phe  Gly  Leu  Thr  Trp
                    275                 280                           285
Glu  Leu  Glu  Asn  Lys  Ala  Leu  Glu  Glu  Gly  Asn  Tyr  Phe  Glu  Met
                    290                 295                           300
Ser  Thr  Tyr  Ser  Thr  Asn  Arg  Thr  Met  Ile  Arg  Ile  Leu  Phe  Ala
                    305                 310                           315
Phe  Val  Ser  Ser  Val  Ala  Arg  Asn  Asp  Thr  Gly  Tyr  Tyr  Thr  Cys
                    320                 325                           330
Ser  Ser  Ser  Lys  His  Pro  Ser  Gln  Ser  Ala  Leu  Val  Thr  Ile  Val
                    335                 340                           345
Glu  Lys  Gly  Phe  Ile  Asn  Ala  Thr  Asn  Ser  Ser  Glu  Asp  Tyr  Glu
                    350                 355                           360
Ile  Asp  Gln  Tyr  Glu  Glu  Phe  Cys  Phe  Ser  Val  Arg  Phe  Lys  Ala
                    365                 370                           375
Tyr  Pro  Gln  Ile  Arg  Cys  Thr  Trp  Thr  Phe  Ser  Arg  Lys  Ser  Phe
                    380                 385                           390
Pro  Cys  Glu  Gln  Lys  Gly  Leu  Asp  Asn  Gly  Tyr  Ser  Ile  Ser  Lys
                    395                 400                           405
Phe  Cys  Asn  His  Lys  His  Gln  Pro  Gly  Glu  Tyr  Ile  Phe  His  Ala
                    410                 415                           420
Ala  Glu  Asn  Asp  Asp  Ala  Gln  Phe  Thr  Lys  Met  Phe  Thr  Leu  Asn
                    425                 430                           435
Ile  Arg  Arg  Lys  Pro  Gln  Val  Leu  Ala  Glu  Ala  Ser  Ala  Ser  Gln
                    440                 445                           450
Ala  Ser  Cys  Phe  Ser  Asp  Gly  Tyr  Pro  Leu  Ser  Trp  Thr  Trp  Lys
                    455                 460                           465
Lys  Cys  Ser  Asp  Lys  Ser  Pro  Asn  Cys  Thr  Glu  Glu  Ile  Thr  Glu
                    470                 475                           480
Gly  Val  Trp  Asn  Arg  Lys  Ala  Asn  Arg  Lys  Val  Phe  Gly  Gln  Trp
                    485                 490                           495
Val  Ser  Ser  Ser  Thr  Leu  Asn  Met  Ser  Glu  Ala  Ile  Lys  Gly  Phe
                    500                 505                           510
Leu  Val  Lys  Cys  Cys  Ala  Tyr  Asn  Ser  Leu  Gly  Thr  Ser  Cys  Glu
                    515                 520                           525
Thr  Ile  Leu  Leu  Asn  Ser  Pro  Gly  Pro  Phe  Pro  Phe  Ile  Gln  Asp
                    530                 535                           540
Asn  Ile  Ser  Phe  Tyr  Ala  Thr  Ile  Gly  Val  Cys  Leu  Leu  Phe  Ile
                    545                 550                           555
Val  Val  Leu  Thr  Leu  Leu  Ile  Cys  His  Lys  Tyr  Lys  Lys  Gln  Phe
                    560                 565                           570
Arg  Tyr  Glu  Ser  Gln  Leu  Gln  Met  Val  Gln  Val  Thr  Gly  Ser  Ser
                    575                 580                           585
Asp  Asn  Glu  Tyr  Phe  Tyr  Val  Asp  Phe  Arg  Glu  Tyr  Glu  Tyr  Asp
                    590                 595                           600
Leu  Lys  Trp  Glu  Phe  Pro  Arg  Glu  Asn  Leu  Glu  Phe  Gly  Lys  Val
```

|     |     |     |     | 605 |     |     |     |     | 610 |     |     |     |     | 615 |
| --- | --- | --- | --- | --- | --- | --- | --- | --- | --- | --- | --- | --- | --- | --- |
| Leu | Gly | Ser | Gly | Ala | Phe | Gly | Lys | Val | Met | Asn | Ala | Thr | Ala | Tyr |
|     |     |     |     | 620 |     |     |     |     | 625 |     |     |     |     | 630 |
| Gly | Ile | Ser | Lys | Thr | Gly | Val | Ser | Ile | Gln | Val | Ala | Val | Lys | Met |
|     |     |     |     | 635 |     |     |     |     | 640 |     |     |     |     | 645 |
| Leu | Lys | Glu | Lys | Ala | Asp | Ser | Ser | Glu | Arg | Glu | Ala | Leu | Met | Ser |
|     |     |     |     | 650 |     |     |     |     | 655 |     |     |     |     | 660 |
| Glu | Leu | Lys | Met | Met | Thr | Gln | Leu | Gly | Ser | His | Glu | Asn | Ile | Val |
|     |     |     |     | 665 |     |     |     |     | 670 |     |     |     |     | 675 |
| Asn | Leu | Leu | Gly | Ala | Cys | Thr | Leu | Ser | Gly | Pro | Ile | Tyr | Leu | Ile |
|     |     |     |     | 680 |     |     |     |     | 685 |     |     |     |     | 690 |
| Phe | Glu | Tyr | Cys | Cys | Tyr | Gly | Asp | Leu | Leu | Asn | Tyr | Leu | Arg | Ser |
|     |     |     |     | 695 |     |     |     |     | 700 |     |     |     |     | 705 |
| Lys | Arg | Glu | Lys | Phe | His | Arg | Thr | Trp | Thr | Glu | Ile | Phe | Lys | Glu |
|     |     |     |     | 710 |     |     |     |     | 715 |     |     |     |     | 720 |
| His | Asn | Phe | Ser | Phe | Tyr | Pro | Thr | Phe | Gln | Ser | His | Pro | Asn | Ser |
|     |     |     |     | 725 |     |     |     |     | 730 |     |     |     |     | 735 |
| Ser | Met | Pro | Gly | Ser | Arg | Glu | Val | Gln | Ile | His | Pro | Asp | Ser | Asp |
|     |     |     |     | 740 |     |     |     |     | 745 |     |     |     |     | 750 |
| Gln | Ile | Ser | Gly | Leu | His | Gly | Asn | Ser | Phe | His | Ser | Glu | Asp | Glu |
|     |     |     |     | 755 |     |     |     |     | 760 |     |     |     |     | 765 |
| Ile | Glu | Tyr | Glu | Asn | Gln | Lys | Arg | Leu | Glu | Glu | Glu | Glu | Asp | Leu |
|     |     |     |     | 770 |     |     |     |     | 775 |     |     |     |     | 780 |
| Asn | Val | Leu | Thr | Phe | Glu | Asp | Leu | Leu | Cys | Phe | Ala | Tyr | Gln | Val |
|     |     |     |     | 785 |     |     |     |     | 790 |     |     |     |     | 795 |
| Ala | Lys | Gly | Met | Glu | Phe | Leu | Glu | Phe | Lys | Ser | Cys | Val | His | Arg |
|     |     |     |     | 800 |     |     |     |     | 805 |     |     |     |     | 810 |
| Asp | Leu | Ala | Ala | Arg | Asn | Val | Leu | Val | Thr | His | Gly | Lys | Val | Val |
|     |     |     |     | 815 |     |     |     |     | 820 |     |     |     |     | 825 |
| Lys | Ile | Cys | Asp | Phe | Gly | Leu | Ala | Arg | Asp | Ile | Met | Ser | Asp | Ser |
|     |     |     |     | 830 |     |     |     |     | 835 |     |     |     |     | 840 |
| Asn | Tyr | Val | Val | Arg | Gly | Asn | Ala | Arg | Leu | Pro | Val | Lys | Trp | Met |
|     |     |     |     | 845 |     |     |     |     | 850 |     |     |     |     | 855 |
| Ala | Pro | Glu | Ser | Leu | Phe | Glu | Gly | Ile | Tyr | Thr | Ile | Lys | Ser | Asp |
|     |     |     |     | 860 |     |     |     |     | 865 |     |     |     |     | 870 |
| Val | Trp | Ser | Tyr | Gly | Ile | Leu | Leu | Trp | Glu | Ile | Phe | Ser | Leu | Gly |
|     |     |     |     | 875 |     |     |     |     | 880 |     |     |     |     | 885 |
| Val | Asn | Pro | Tyr | Pro | Gly | Ile | Pro | Val | Asp | Ala | Asn | Phe | Tyr | Lys |
|     |     |     |     | 890 |     |     |     |     | 895 |     |     |     |     | 900 |
| Leu | Ile | Gln | Asn | Gly | Phe | Lys | Met | Asp | Gln | Pro | Phe | Tyr | Ala | Thr |
|     |     |     |     | 905 |     |     |     |     | 910 |     |     |     |     | 915 |
| Glu | Glu | Ile | Tyr | Ile | Ile | Met | Gln | Ser | Cys | Trp | Ala | Phe | Asp | Ser |
|     |     |     |     | 920 |     |     |     |     | 925 |     |     |     |     | 930 |
| Arg | Lys | Arg | Pro | Ser | Phe | Pro | Asn | Leu | Thr | Ser | Phe | Leu | Gly | Cys |
|     |     |     |     | 935 |     |     |     |     | 940 |     |     |     |     | 945 |
| Gln | Leu | Ala | Asp | Ala | Glu | Glu | Ala | Met | Tyr | Gln | Asn | Val | Asp | Gly |
|     |     |     |     | 950 |     |     |     |     | 955 |     |     |     |     | 960 |
| Arg | Val | Ser | Glu | Cys | Pro | His | Thr | Tyr | Gln | Asn | Arg | Arg | Pro | Phe |
|     |     |     |     | 965 |     |     |     |     | 970 |     |     |     |     | 975 |
| Ser | Arg | Glu | Met | Asp | Leu | Gly | Leu | Leu | Ser | Pro | Gln | Ala | Gln | Val |
|     |     |     |     | 980 |     |     |     |     | 985 |     |     |     |     | 990 |
| Glu | Asp | Ser |     |     |     |     |     |     |     |     |     |     |     |     |
|     |     | 993 |     |     |     |     |     |     |     |     |     |     |     |     |

( 2 ) INFORMATION FOR SEQ ID NO:3:

( i ) SEQUENCE CHARACTERISTICS:
        ( A ) LENGTH: 18 Nucleotides
        ( B ) TYPE: nucleic acid
        ( C ) STRANDEDNESS: single stranded
        ( D ) TOPOLOGY: linear ( x i ) SEQUENCE DESCRIPTION: SEQ ID NO:3:

CCCTCGGATG CCGCCTCG   18

( 2 ) INFORMATION FOR SEQ ID NO:4:

( i ) SEQUENCE CHARACTERISTICS:
        ( A ) LENGTH: 18 Nucleotides
        ( B ) TYPE: nucleic acid
        ( C ) STRANDEDNESS: single stranded
        ( D ) TOPOLOGY: linear ( x i ) SEQUENCE DESCRIPTION: SEQ ID NO:4:

GCGCGCCAAC GCCGGCAT   18

( 2 ) INFORMATION FOR SEQ ID NO:5:

( i ) SEQUENCE CHARACTERISTICS:
        ( A ) LENGTH: 18 Nucleotides
        ( B ) TYPE: nucleic acid
        ( C ) STRANDEDNESS: single stranded
        ( D ) TOPOLOGY: linear ( x i ) SEQUENCE DESCRIPTION: SEQ ID NO:5:

ATTTGTAATA GTCCCAAA   18

( 2 ) INFORMATION FOR SEQ ID NO:6:

( i ) SEQUENCE CHARACTERISTICS:
        ( A ) LENGTH: 18 Nucleotides
        ( B ) TYPE: nucleic acid
        ( C ) STRANDEDNESS: single stranded
        ( D ) TOPOLOGY: linear ( x i ) SEQUENCE DESCRIPTION: SEQ ID NO:6:

CGAGGCGGCA TCCGAGGG   18

( 2 ) INFORMATION FOR SEQ ID NO:7:

( i ) SEQUENCE CHARACTERISTICS:
        ( A ) LENGTH: 18 Nucleotides
        ( B ) TYPE: nucleic acid
        ( C ) STRANDEDNESS: single stranded
        ( D ) TOPOLOGY: linear ( x i ) SEQUENCE DESCRIPTION: SEQ ID NO:7:

ATGCCGGCGT TGGCGCGC   18

( 2 ) INFORMATION FOR SEQ ID NO:8:

( i ) SEQUENCE CHARACTERISTICS:
        ( A ) LENGTH: 18 Nucleotides
        ( B ) TYPE: nucleic acid
        ( C ) STRANDEDNESS: single stranded
        ( D ) TOPOLOGY: linear ( x i ) SEQUENCE DESCRIPTION: SEQ ID NO:8:

TTTGGGACTA TTACAAAT   18

( 2 ) INFORMATION FOR SEQ ID NO:9:

```
( i ) SEQUENCE CHARACTERISTICS:
        ( A ) LENGTH: 18 Nucleotides
        ( B ) TYPE: nucleic acid
        ( C ) STRANDEDNESS: single stranded
        ( D ) TOPOLOGY: linear ( x i ) SEQUENCE DESCRIPTION: SEQ ID NO:9:

CTCCGGCTGA GGCCCTCC      18

( 2 ) INFORMATION FOR SEQ ID NO:10:

( i ) SEQUENCE CHARACTERISTICS:
            ( A ) LENGTH: 18 Nucleotides
            ( B ) TYPE: nucleic acid
            ( C ) STRANDEDNESS: single stranded
            ( D ) TOPOLOGY: linear ( x i ) SEQUENCE DESCRIPTION: SEQ ID NO:10:

ACCCAGGCGT CCGCGGCA      18

( 2 ) INFORMATION FOR SEQ ID NO:11:

( i ) SEQUENCE CHARACTERISTICS:
            ( A ) LENGTH: 18 Nucleotides
            ( B ) TYPE: nucleic acid
            ( C ) STRANDEDNESS: single stranded
            ( D ) TOPOLOGY: linear ( x i ) SEQUENCE DESCRIPTION: SEQ ID NO:11:

CAGAAACGTA TTATTTCA      18
```